(12) United States Patent
Takahashi et al.

(10) Patent No.: US 10,240,974 B2
(45) Date of Patent: Mar. 26, 2019

(54) INFRARED PROJECTOR AND INFRARED OBSERVATION SYSTEM

(71) Applicant: Sharp Kabushiki Kaisha, Sakai, Osaka (JP)

(72) Inventors: Koji Takahashi, Sakai (JP); Hidenori Kawanishi, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 0 days.

(21) Appl. No.: 15/564,449

(22) PCT Filed: Mar. 16, 2016

(86) PCT No.: PCT/JP2016/058309
§ 371 (c)(1),
(2) Date: Oct. 5, 2017

(87) PCT Pub. No.: WO2016/163216
PCT Pub. Date: Oct. 13, 2016

(65) Prior Publication Data
US 2018/0080816 A1 Mar. 22, 2018

(30) Foreign Application Priority Data

Apr. 10, 2015 (JP) .................................. 2015-081264

(51) Int. Cl.
*G01J 5/00* (2006.01)
*G01J 1/08* (2006.01)
(Continued)

(52) U.S. Cl.
CPC .............. *G01J 1/08* (2013.01); *G01J 1/0411* (2013.01); *G01J 1/0425* (2013.01); *G01J 1/44* (2013.01);
(Continued)

(58) Field of Classification Search
CPC ...... H04N 5/2256; H04N 5/33; H04N 5/2252; H04N 5/2254; G02B 6/008; G02B 3/0056;
(Continued)

(56) References Cited

U.S. PATENT DOCUMENTS 9,106,045 B2 * 8/2015 Galbraith ................ H01S 3/005
2003/0066965 A1 4/2003 Abel et al.
(Continued)

FOREIGN PATENT DOCUMENTS

JP 09-231806 A 9/1997
JP 10-325798 A 12/1998
(Continued)

OTHER PUBLICATIONS

Official Communication issued in International Patent Application No. PCT/JP2016/058309, dated Jun. 14, 2016.
(Continued)

*Primary Examiner* — Kiho Kim
(74) *Attorney, Agent, or Firm* — Keating & Bennett, LLP

(57) ABSTRACT

An infrared projector and an infrared observation system by which unevenness of wavelengths in a projection pattern is reduced are provided. An infrared projector (100) is provided with infrared semiconductor laser elements (11a to 11d) that emit near-infrared laser light beams (L1a, L1b, L1c, and L1d), a scattering member (51) that receives and scatters the near-infrared laser light beams, and a projecting member (61) that projects the near-infrared laser light beams scattered by the scattering member.

20 Claims, 13 Drawing Sheets

(51) Int. Cl.
*G01N 21/01* (2006.01)
*G01J 1/04* (2006.01)
*G01J 1/44* (2006.01)
*G02B 5/02* (2006.01)
*G02B 7/02* (2006.01)
*G02B 7/182* (2006.01)
*G02B 27/09* (2006.01)
*G03B 15/02* (2006.01)
*H04N 5/33* (2006.01)
*G02B 19/00* (2006.01)
*H01S 5/00* (2006.01)
*H04N 5/225* (2006.01)
*F21V 8/00* (2006.01)
*H01S 5/022* (2006.01)
*H01S 5/40* (2006.01)
*G03B 15/03* (2006.01)

(52) U.S. Cl.
CPC ............. *G01N 21/01* (2013.01); *G02B 5/021* (2013.01); *G02B 7/02* (2013.01); *G02B 7/023* (2013.01); *G02B 7/182* (2013.01); *G02B 19/0014* (2013.01); *G02B 19/0057* (2013.01); *G02B 27/0916* (2013.01); *G03B 15/02* (2013.01); *H01S 5/005* (2013.01); *H04N 5/2252* (2013.01); *H04N 5/2254* (2013.01); *H04N 5/2256* (2013.01); *H04N 5/33* (2013.01); *G02B 6/0006* (2013.01); *G02B 6/0008* (2013.01); *G03B 15/03* (2013.01); *G03B 2215/0567* (2013.01); *G03B 2215/0589* (2013.01); *H01S 5/02212* (2013.01); *H01S 5/02284* (2013.01); *H01S 5/4012* (2013.01)

(58) Field of Classification Search
CPC .......... G02B 19/00; G02B 5/021; G02B 7/02; G02B 7/182; G02B 19/0014; G02B 19/0057; G02B 27/0916; G02B 6/0006; G02B 6/0008; G01J 1/08; G01J 1/0411; G01J 1/0425; G01J 1/44; G01N 21/01; G03B 15/02; G03B 15/03; H01S 5/005
See application file for complete search history.

(56) References Cited

U.S. PATENT DOCUMENTS

| 2004/0169857 | A1* | 9/2004 | Acosta | G01N 21/278 356/328 |
| 2006/0238617 | A1 | 10/2006 | Tamir | |
| 2011/0044070 | A1 | 2/2011 | Takahashi | |
| 2011/0109232 | A1* | 5/2011 | Schulz | G01J 1/02 315/151 |
| 2013/0314937 | A1 | 11/2013 | Takahashi et al. | |
| 2013/0327964 | A1 | 12/2013 | Otsuka | |
| 2015/0168555 | A1* | 6/2015 | Herschbach | G01S 17/48 356/5.01 |
| 2015/0375672 | A1 | 12/2015 | Takahashi | |

FOREIGN PATENT DOCUMENTS

| JP | 2001-333423 A | 11/2001 |
| JP | 2003-237467 A | 8/2003 |
| JP | 2008-527806 A | 7/2008 |
| JP | 2011-065979 A | 3/2011 |
| JP | 2011-157023 A | 8/2011 |
| JP | 2012-198276 A | 10/2012 |
| JP | 2013-090706 A | 5/2013 |
| JP | 2013-246943 A | 12/2013 |
| JP | 2013-257996 A | 12/2013 |
| JP | 2014-049369 A | 3/2014 |
| JP | 2014-170758 A | 9/2014 |
| JP | 2016-011039 A | 1/2016 |

OTHER PUBLICATIONS

Takahashi et al., "Illumination Device and Observation System," U.S. Appl. No. 15/564,448, filed Oct. 5, 2017.

* cited by examiner (a)

(b)

INFRARED PROJECTOR AND INFRARED OBSERVATION SYSTEM

TECHNICAL FIELD

The present invention relates to a projector and an observation system using the projector, and, particularly relates to a projector using infrared rays and an observation system using the projector.

BACKGROUND ART

In PTL 1, a dark place monitoring device in which a plurality of LEDs serving as light sources are arranged in both sides of a lens of a monitoring camera and which radiates infrared rays from the LEDs onto an object is described as a projector that projects infrared rays.

CITATION LIST

Patent Literature

PTL 1: Japanese Unexamined Patent Application Publication No. 2001-333423 (published on Nov. 30, 2001)

SUMMARY OF INVENTION

Technical Problem

However, in a case where the plurality of LEDs are independently turned on in the dark place monitoring device described in PTL 1, there is a problem that projection patterns of the plurality of light sources do not overlap due to a difference of inclination between the plurality of light sources and deviation is caused. The deviation of the projection patterns is remarkable in a case where projection is performed to a distant place by using light whose spread angle from a light source is small.

The aforementioned problem can be caused also in a case where visible light is projected. However, in a case where an infrared light beam is projected, it is impossible to confirm a projection pattern thereof with the naked eye, and it is necessary to use a device such as an infrared camera, so that it is difficult to detect deviation of projection patterns. Thus, the above-described problem becomes more serious.

The invention is made in view of the above-described problem, and an object thereof is to provide an infrared projector and an infrared observation system by which uniform projection patterns are able to be obtained.

Solution to Problem

In order to solve the aforementioned problem, an infrared projector according to an aspect of the invention includes: a plurality of laser light sources that emit near-infrared laser light beams; a scattering member that receives the near-infrared laser light beams emitted from the plurality of laser light sources and scatters the received near-infrared laser light beams; and a projecting member that projects the near-infrared laser light beams scattered by the scattering member.

Advantageous Effects of Invention

According to an infrared projector according to an aspect of the invention, it is possible to provide an infrared projector by which uniform projection patterns are able to be obtained.

DESCRIPTION OF EMBODIMENTS

Embodiment 1

Hereinafter, an embodiment of the invention will be described in detail by using FIG. 1 to FIG. 5. In each of the drawings, it is set that an x direction is a direction of one side of a scattering member 51 illustrated in FIG. 2 and a left direction in a case where the direction of the one side is a right-and-left direction is a positive direction. Note that, a right direction in the case where the direction of the one side is the right-and-left direction may be the positive direction.

Figure 2:
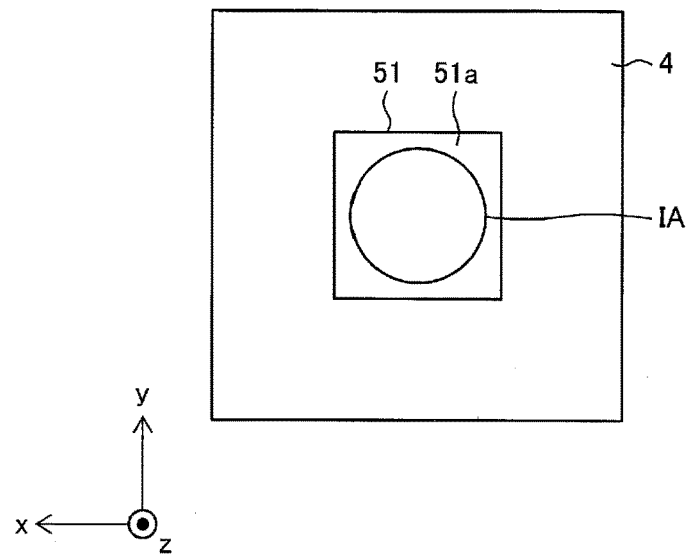
FIG. 2 is a view illustrating a condensing spot formed on a front surface of a scattering member provided in the infrared projector illustrated in FIG. 1.

On the other hand, it is set that a y direction is a direction of a side perpendicular to the x direction among sides of the scattering member 51 illustrated in FIG. 2 and an upper direction in a case where the direction of the side is an up-and-down direction is a positive direction. Note that, a lower direction in the case where the direction of the side is the up-and-down direction may be the positive direction.

Figure 1:
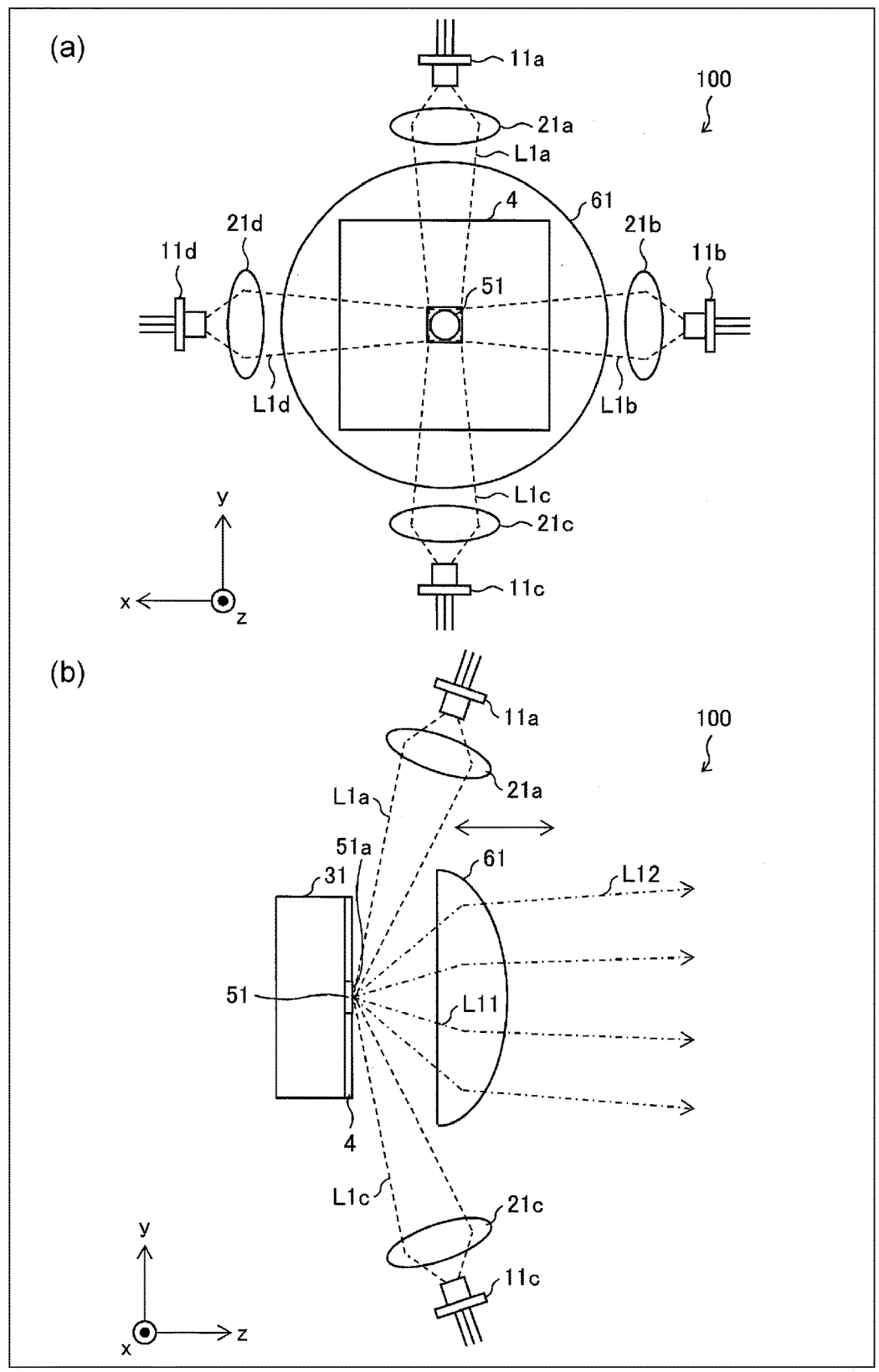
FIG. 1 is a schematic view of an infrared projector according to Embodiment 1 of the invention, in which (a) is a view which is viewed from a +z direction and (b) is a view which is viewed from +x direction.

Furthermore, it is set that a z direction is a direction perpendicular to both the x direction and the y direction and a direction in which projected light L12 is projected is a positive direction in (b) of FIG. 1.

(Outline of Infrared Projector 100)

FIG. 1 is a view illustrating an outline of an infrared projector 100 according to the present embodiment, in which (a) is a view which is viewed from the +z direction and (b) is a view which is viewed from the +x direction. As illustrated in (a) and (b) of FIG. 1, the infrared projector 100 includes four infrared semiconductor laser elements 11a, 11b, 11c, and 11d, four condenser lenses 21a, 21b, 21c, and 21d, a supporting base 31, a light absorbing material 4, the scattering member 51, and a projecting member 61.

Note that, the infrared semiconductor laser elements 11b and 11d and the condenser lenses 21b and 21d are omitted in (b) of FIG. 1

The infrared semiconductor laser elements 11a to 11d are laser light sources which emit near-infrared laser light beams L1a to L1d, respectively. Each of the infrared semiconductor laser elements 11a to 11d is attached to a heat sink (not illustrated) for heat radiation, and connected to a power source circuit (not illustrated) for drive.

In the present embodiment, an output of each of the infrared semiconductor laser elements 11a to 11d is 1 W. Moreover, a shape of an emitting spot of each of the near-infrared laser light beams on an emitting end surface of each of the infrared semiconductor laser elements 11a to 11d, from which the near-infrared laser light beam is emitted, is an ellipse whose minor axis is 1 to 2 μm and whose major axis is 2 to 50 μm, for example. At this time, an area of the emitting spot is $0.5\pi$ to $25\pi$ μm$^2$.

A peak wavelength of each of the near-infrared laser light beams L1a to L1d may be not less than 740 nm and not more than 1000 nm. In the present embodiment, the peak wavelengths of the near-infrared laser light beams L1a to L1d are 780 nm, 800 nm, 820 nm, and 840 nm, respectively.

Note that, a numerical value range of "not less than 740 nm and not more than 1000 nm" indicates a value with which a range of a wavelength of each of near-infrared light beams is exemplified. Accordingly, the peak wavelength of each of the near-infrared laser light beams L1a to L1d only needs to be within the range of the wavelength of the near-infrared light beam, and is not necessarily limited to be not less than 740 nm and not more than 1000 nm.

The condenser lenses 21a to 21d are members that condense the near-infrared laser light beams L1a to L1d. Specifically, the condenser lens 21a, the condenser lens 21b, the condenser lens 21c, and the condenser lens 21d condense the near-infrared laser light beam L1a, the near-infrared laser light beam L1b, the near-infrared laser light beam L1c, and the near-infrared laser light beam L1d, respectively. In the present embodiment, the condenser lenses 21a to 21d are convex lenses made of glass.

The supporting base 31 is a base that supports the light absorbing material 4 and the scattering member 51 which will be described below. In the present embodiment, the supporting base 31 is made of aluminum. Note that, the supporting base 31 may be configured by using another material, for example, such as another metal or highly heat-conductive ceramic.

There is a possibility that temperature of the scattering member 51 supported by the supporting base 31 becomes high when the near-infrared laser light beams L1a to L1d enter as described below. In order to improve cooling efficiency of the scattering member 51, the supporting base 31 may be provided as a heat radiation fin.

The light absorbing material 4 suppresses scattering of light other than light entering the scattering member 51 described below. In the present embodiment, the light absorbing material 4 is carbon particles applied to the supporting base 31.

The scattering member 51 is a member that receives the near-infrared laser light beams L1a to L1d emitted from the infrared semiconductor laser elements 11a to 11d and scatters the received near-infrared laser light beams. The scattering member 51 has a front surface 51a which is a surface that the near-infrared laser light beams L1a to L1d enter.

In the present embodiment, the scattering member 51 is a member that includes a surface having predetermined roughness by which the entered near-infrared laser light beams L1a to L1d are isotropically scattered. Specifically, the scattering member 51 has the front surface 51a whose roughness satisfies Ra=1 μm. Moreover, in the present embodiment, the scattering member 51 is made of metal. Specifically, a material of the scattering member 51 is aluminum.

Note that, a form of the scattering member 51 is not limited to aluminum having unevenness on a front surface thereof as described in the present embodiment, that is, a member causing surface scattering. A member causing volume scattering may be used as the scattering member 51. As the member causing volume scattering, for example, it is possible to use a scattering member in which, in a member which is transparent to infrared rays, such as glass, a scattering material (a filler or the like) whose refractive index is different from that of the glass is dispersed, or the like.

The projecting member 61 is a member that projects the near-infrared laser light beams scattered by the scattering member 51. In the present embodiment, the projecting member 61 is a lens. More specifically, the projecting member 61 is a plano-convex lens made of glass. The plano-convex lens is a lens having a spherical surface on one side and a flat surface on the other side. An optical axis of the projecting member 61 is perpendicular to the front surface 51a of the scattering member 51. In other words, the z direction described above may be understood as a direction of the optical axis of the projecting member 61.

The projecting member 61 may be a lens having any curved surface such as a free curved surface. Moreover, a material of the projecting member 61 may be quartz, sapphire, resin, or the like.

The projecting member 61 forms an image of a condensing spot IA of the near-infrared laser light beams L1a to L1d, which is on the scattering member 51, at a position distant from the projecting member 61 by a predetermined distance.

Moreover, the infrared projector 100 further includes a moving mechanism (for example, a moving mechanism 71 in FIG. 4 or a moving mechanism 72 in FIG. 5) that adjusts relative positions of the projecting member 61 and the scattering member 51 as to the z direction. In the present embodiment, the relative position of the projecting member 61 with respect to the scattering member 51 is adjusted so that a spread angle of the near-infrared laser light beams projected from the projecting member 61 becomes minimum.

(Operation of Infrared Projector 100)

The infrared projector 100 has a configuration in which the near-infrared laser light beams L1a to L1d enter the front surface (predetermined surface) 51a of the scattering member 51 and scattered light L11 scattered to a side of the front surface 51a is projected by the projecting member 61. Hereinafter, the configuration is referred to as a configuration of a reflecting type. An operation of the infrared projector 100 will be described below.

As illustrated in (a) of FIG. 1, the infrared semiconductor laser elements 11a to 11d emit the near-infrared laser light beams L1a to L1d toward the scattering member 51 from four directions that intersect at right angles in a case of being viewed from the +z direction. The near-infrared laser light beams L1a to L1d are condensed on the front surface 51a of the scattering member 51 by the condenser lenses 21a to 21d.

FIG. 2 is a view illustrating the condensing spot IA that is formed by the near-infrared laser light beams L1a to L1d (refer to (a) of FIG. 1) condensed on the front surface 51a of the scattering member 51. As illustrated in FIG. 2, the near-infrared laser light beams L1a to L1d condensed by the condenser lenses 21a to 21d form the condensing spot IA on the front surface 51a. In the present embodiment, a shape of the condensing spot IA is a round shape whose diameter is 1 mm.

Figure 3:
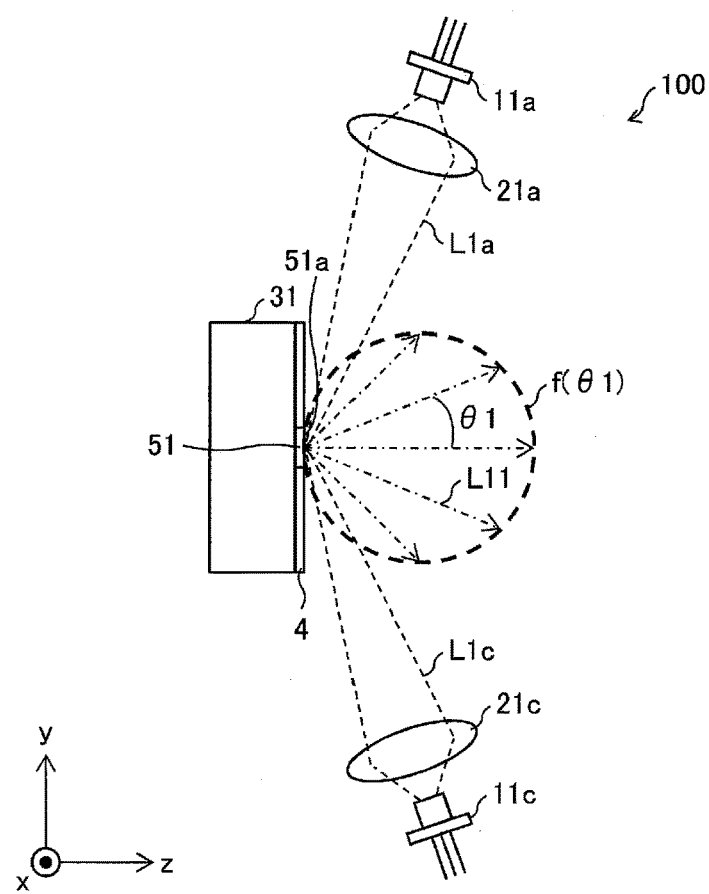
FIG. 3 is a view illustrating a state in which near-infrared laser light beams are scattered by the scattering member illustrated in FIG. 2.

FIG. 3 is a view illustrating a state in which the near-infrared laser light beams are scattered by the front surface 51a of the scattering member 51. Note that, since FIG. 3 is a view illustrated at an angle similar to that of (b) of FIG. 1, the near-infrared laser light beams L1b and L1d are omitted.

The near-infrared laser light beams L1a to L1d condensed on the front surface 51a of the scattering member 51 are isotropically scattered to the side of the front surface 51a as the scattered light L11 by fine unevenness, provided in the front surface 51a, regardless of the entering directions.

Intensity distribution of the scattered light L11 scattered by the front surface 51a of the scattering member 51 obeys Lambert distribution. That is, in a case where intensity of the scattered light L11 scattered in a direction perpendicular to the front surface 51a is set as I, intensity of the scattered light L11 scattered in a direction inclining by an angle $\theta 1$ from the direction perpendicular to the front surface 51a is $I \times \cos \theta 1$.

As illustrated in (b) of FIG. 1, the projecting member 61 projects the scattered light L11, scattered by the scattering member 51, to a side opposite to a side, which the scattered light L11 enters, as projected light L12.

(Configuration of Moving Mechanism)

Figure 4:
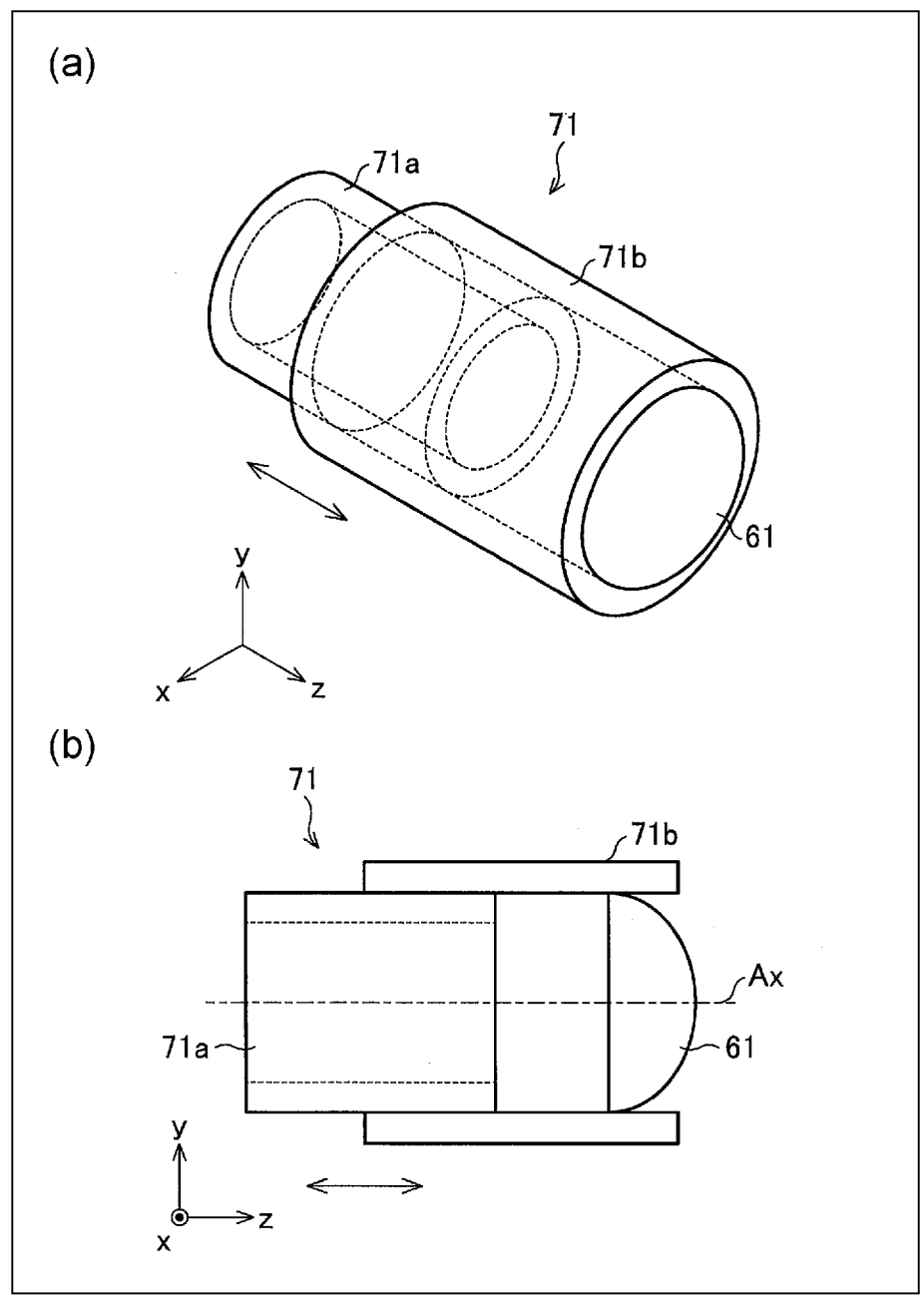
FIG. 4 is a view illustrating an example of a moving mechanism that moves a projecting member, in which (a) is a perspective through view and (b) is a sectional view.

FIG. 4 is a view illustrating the moving mechanism 71 which is an example of a moving mechanism that moves the projecting member 61, in which (a) is a perspective through view and (b) is a sectional view. As illustrated in (a) and (b) of FIG. 4, the moving mechanism includes a housing 71a and a lens holder 71b.

The housing 71a is a tubular member that accommodates the supporting base 31, the light absorbing material 4, and the scattering member 51. The lens holder 71b is a tubular member to one end of which the projecting member 61 is fixed. The optical axis of the projecting member 61 is coincident with a center axis of the housing 71a and a center axis Ax of the lens holder 71b. Moreover, a hole or a slit through which the near-infrared laser light beams L1a to L1d pass is provided in the housing 71a or the lens holder 71b.

The lens holder 71b is configured so as to be able to slide on an outside of the housing 71a. By sliding the lens holder 71b, it is possible to move the projecting member 61 with respect to the scattering member 51 accommodated in the housing 71a.

Note that, in the aforementioned example, each of the housing 71a and the lens holder 71b is a cylinder. However, shapes of the housing 71a and the lens holder 71b may be shapes other than cylindrical ones, such as square-shaped tubes, for example.

Figure 5:
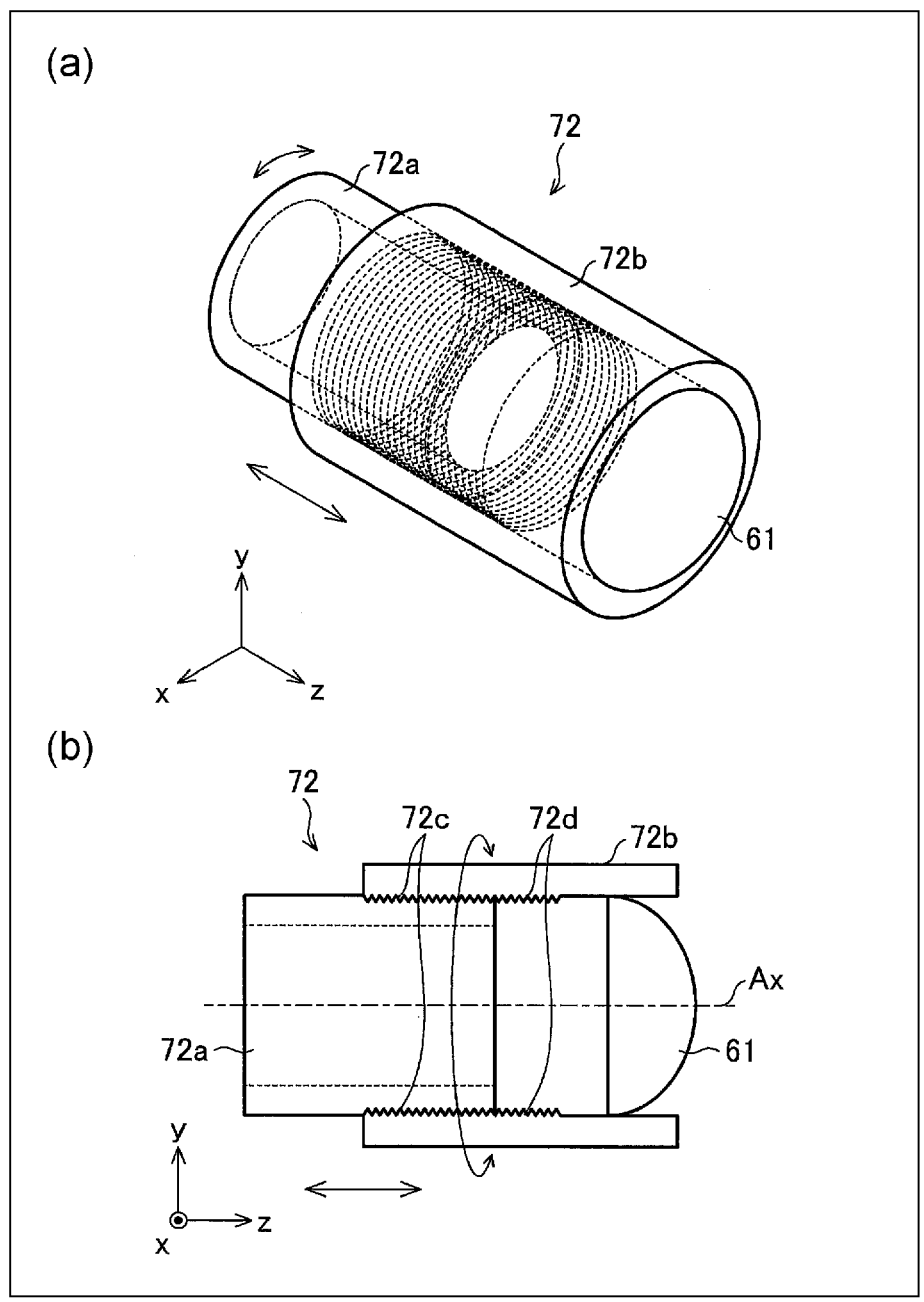
FIG. 5 is a view illustrating another example of the moving mechanism that moves the projecting member, in which (a) is a perspective through view and (b) is a sectional view.

FIG. 5 is a view illustrating the moving mechanism 72 that is an example of the moving mechanism that moves the projecting member 61, which is different from the moving mechanism 71 illustrated in FIG. 4, in which (a) is a perspective through view and (b) is a sectional view. As illustrated in (a) and (b) of FIG. 5, the moving mechanism includes a housing 72a and a lens holder 72b.

The housing 72a is a tubular member that accommodates the supporting base 31, the light absorbing material 4, and the scattering member 51 in an inside thereof. A screw groove 72c is formed on an outer surface of the housing 72a.

The lens holder 72b is a tubular member to one end of which the projecting member 61 is fixed. A thread 72d is formed on an inner surface of the lens holder 72b.

The housing 72a and the lens holder 72b are engaged with each other with the use of the screw groove 72c and the thread 72d. By rotating the lens holder 72b, it is possible to move the projecting member 61, which is fixed to the one end of the lens holder 72b, in the z direction with respect to the scattering member 51 accommodated in the housing 72a. In addition, a hole or a slit through which the near-infrared laser light beams L1a to L1d pass is provided in the housing 72a or the lens holder 72b.

In the present embodiment, the position of the projecting member 61 with respect to the scattering member 51 is adjusted so that spread of the projected light from the projecting member 61 becomes minimum.

(Effect of Infrared Projector 100)

In the infrared projector 100, the near-infrared laser light beams L1a to L1d emitted from the infrared semiconductor laser elements 11a to 11d are condensed in an overlapping manner on the front surface 51a of the scattering member 51, and isotropically scattered as the scattered light L11. The scattered light L11 is light in which the near-infrared laser light beams L1a to L1d whose peak wavelengths are different are mixed.

At this time, the condensing spot IA formed on the front surface 51a of the scattering member 51 functions as a pseudo-light source that emits the scattered light L11 in which the near-infrared laser light beams L1a to L1d whose peak wavelengths are different are mixed. The scattered light L11 from the pseudo-light source is projected to an outside as the projected light L12 by the projecting member 61 which is a convex lens.

Thus, a projection pattern of the infrared projector 100 is configured by the projected light from the single pseudo-light source, so that the infrared projector 100 is an infrared projector by which deviation of projection patterns of a plurality of near-infrared laser light beams is not caused in the projection patterns. Furthermore, in a case where wavelengths of a plurality of near-infrared light beams are different, the infrared projector 100 is an infrared projector by which unevenness of wavelengths is not caused in a projection pattern.

Moreover, in a case where wavelengths of a plurality of near-infrared laser light beams are different from each other, when the near-infrared laser light beams are mixed, temporal coherency of the mixed near-infrared laser light beams as a whole is lowered. Thus, it is possible to suppress occurrence of a projected image which is in a moire state, which is caused when the plurality of near-infrared laser light beams interfere with each other, thus making it possible to obtain a more uniform projection pattern. This point applies to the following other exemplary embodiments similarly.

Moreover, an area of the condensing spot IA that functions as the pseudo-light source emitting the scattered light L11 is enlarged compared with the area of the emitting spot of each of the emitting end surfaces from which the near-infrared laser light beams L1a to L1d are emitted. Specifically, the area of the emitting spot is $0.5\pi$ to $25\pi$ $\mu m^2$, as described above. On the other hand, the area of the condensing spot IA is $0.25\pi$ $mm^2$.

Accordingly, when calculation is performed on the basis of the area of the emitting spot and the area of the condensing spot IA, energy density of the scattered light L11 is $2\times10^{-6}$ times to $1\times10^{-4}$ times of energy density of each of the near-infrared laser light beams L1a to L1d emitted from the infrared semiconductor laser elements 11a to 11d.

Thus, in a case where the projected light L12 projected from the infrared projector 100 is condensed again by a lens or the like in an outside of the infrared projector 100, the energy density hardly becomes high. Therefore, risk of a case where a person sees the projected light from the infrared projector 100 directly or through a lens is reduced.

In the infrared projector 100, the position of the projecting member 61 is adjusted by the moving mechanism so that the spread angle of the light projected by the projecting member 61 becomes minimum. Therefore, the infrared projector 100 is able to project an infrared light beam to a distant place.

Moreover, in the infrared projector 100, by modulating intensity of a near-infrared laser light beam having one or more wavelengths, it is possible to perform infrared communication. In this case, it is preferable that a side receiving infrared rays is able to detect a signal at any position on a light-receiving surface that an infrared light beam reaches. When there is a difference of positions between an infrared light beam by which the light-receiving surface is illuminated at a time of the infrared communication and an infrared light beam in which the signal exists, it is difficult to correctly detect the signal, resulting in that a communication error is caused (quality of communication is deteriorated). By performing communication by the present infrared projector, it is possible to perform high-quality communication in which a communication error is reduced.

Embodiment 2

Another embodiment of the invention will be described as follows on the basis of FIG. 6 to FIG. 9. Note that, for convenience of description, the same reference signs are assigned to members having the same functions as those of the members described in the above-described embodiment, and description thereof is omitted.

In an infrared projector 200 according to the present embodiment, a rear surface 52b of a scattering member 52, which is transparent to infrared rays, functions as a pseudo-light source of a near-infrared laser light beam having a plurality of peak wavelengths. In addition, a concave mirror is provided as a projecting member.

(Outline of Infrared Projector 200)

Figure 6:
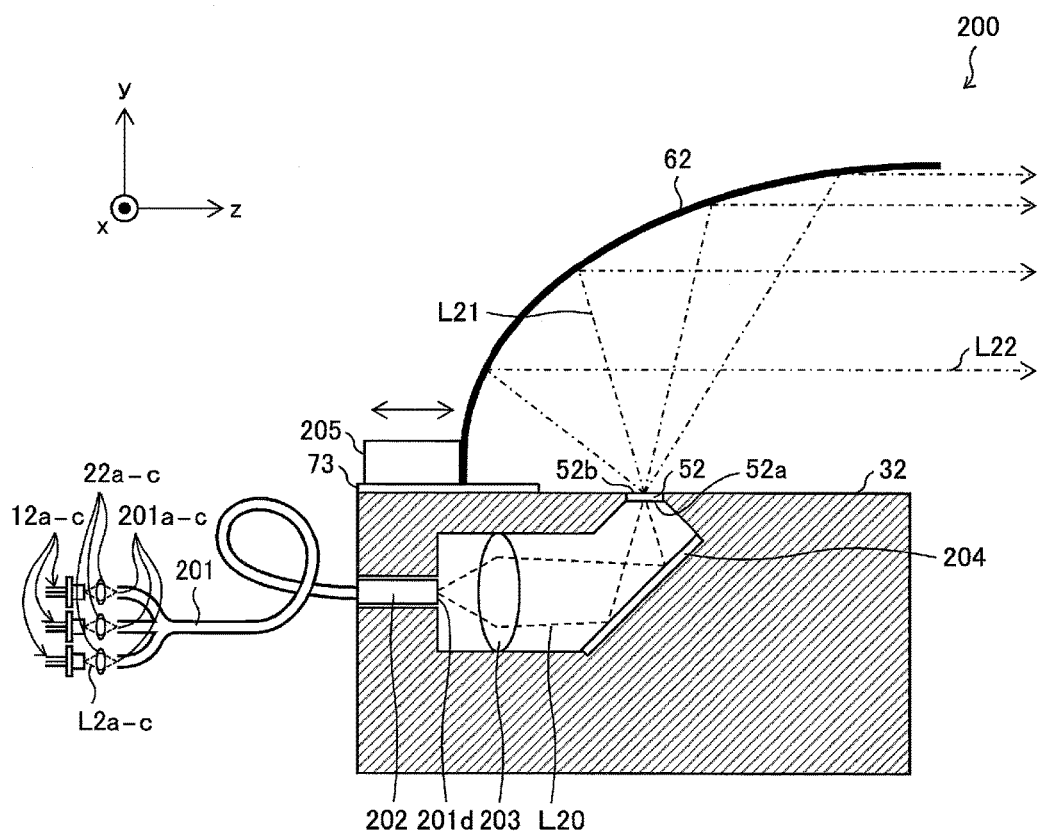
FIG. 6 is a schematic view of an infrared projector according to Embodiment 2 of the invention.

FIG. 6 is a view illustrating an outline of the infrared projector 200. As illustrated in FIG. 6, the infrared projector 200 is provided with three infrared semiconductor laser elements 12a, 12b, and 12c, three condenser lenses 22a, 22b, and 22c, an optical transmission path 201, a fixing member 202, a condenser lens 203, a reflecting mirror 204, the scattering member 52, a projecting member 62, a housing 32, a supporting member 205, and a moving mechanism 73.

The infrared semiconductor laser elements 12a to 12c are laser light sources which emit near-infrared laser light beams L2a to L2c, respectively. Each of the infrared semiconductor laser elements 12a to 12c is attached to a heat sink (not illustrated) for heat radiation, and connected to a power source circuit (not illustrated) for drive.

In the present embodiment, an output of each of the infrared semiconductor laser elements 12a to 12c is 0.5 W. Moreover, in the present embodiment, peak wavelengths of the near-infrared laser light beams L2a to L2c are 800 nm, 900 nm, and 1000 nm, respectively.

The condenser lenses 22a to 22c are members that condense the near-infrared laser light beams L2a to L2c. In the present embodiment, the condenser lenses 22a to 22c are convex lenses made of glass.

The optical transmission path 201 is a member that transmits the near-infrared laser light beams L2a to L2c in a mixed manner. In the present embodiment, the optical transmission path 201 is a multimode fiber having a round-shaped core. Moreover, the optical transmission path 201 includes three entering ends 201a, 201b, and 201c and one emitting end 201d.

The fixing member 202 is a member by which the optical transmission path 201 is fixed. The condenser lens 203 is a member that condenses a near-infrared laser light beam L20 emitted from the emitting end 201d of the optical transmission path 201. In the present embodiment, the condenser lens 203 is a convex lens made of glass.

The reflecting mirror 204 is a member that reflects the near-infrared laser light beam L20 condensed by the condenser lens 203. The reflecting mirror 204 may be a plate covered with metal such as aluminum or a mirror made of metal. Alternatively, the reflecting mirror 204 may be a multilayer-film reflecting mirror covered with a dielectric.

The scattering member 52 is a member that is transparent to the near-infrared laser light beams L2a to L2c. Glass, sapphire, quartz, or the like is able to be used as a material of the scattering member 52.

The scattering member 52 includes a front surface 52a that the near-infrared laser light beam L20 enters and the rear surface 52b opposed to the front surface 52a. The scattering member 52 is a member in which at least one of the front surface 52a and the rear surface 52b is a rough surface and which is transparent to infrared rays, and is a member like a so-called frosted glass.

The projecting member 62 is a member that projects scattered light L21 scattered by the scattering member 52 toward a predetermined direction. In the present embodiment, the projecting member 62 is a concave mirror. More specifically, the projecting member 62 is a concave mirror having a shape obtained by cutting out a part of a paraboloid of revolution. Moreover, the projecting member 62 may be a concave mirror having any curved surface such as a free curved surface.

The housing 32 is a member that accommodates the condenser lens 203 and the reflecting mirror 204 in an inside thereof and holds the scattering member 52 by a periphery of the scattering member 52. In the present embodiment, a material of the housing 32 is metal.

The supporting member 205 is a member that supports the projecting member 62. The moving mechanism 73 is a moving mechanism by which the projecting member 62 is moved. A specific configuration of the moving mechanism 73 will be described below.

(Operation of Infrared Projector 200)

The infrared projector 200 has a configuration in which the near-infrared laser light beam L20 is caused to enter the front surface (predetermined surface) 52a of the scattering member 52 and the scattered light L21 scattered to a side of the rear surface 52b opposed to the front surface 52a is projected by the projecting member 62. Hereinafter, the configuration is referred to as a configuration of a transmitting type. An operation of the infrared projector 200 will be described below.

As illustrated in FIG. 6, the infrared semiconductor laser elements 12a to 12c emit the near-infrared laser light beams L2a to L2c toward the entering ends 201a to 201c of the optical transmission path 201. The near-infrared laser light beams L2a to L2c enter an inside of the optical transmission path 201 from the entering ends 201a to 201c of the optical transmission path 201 via the condenser lenses 22a to 22c. The near-infrared laser light beams L2a to L2c which have entered the inside of the optical transmission path 201 are mixed in the inside of the optical transmission path 201, and emitted from the emitting end 201d of the optical transmission path 201 as the near-infrared laser light beam L20. The near-infrared laser light beam L20 is condensed on the front surface 52a of the scattering member 52 by the condenser lens 203 and the reflecting mirror 204.

Figure 7:
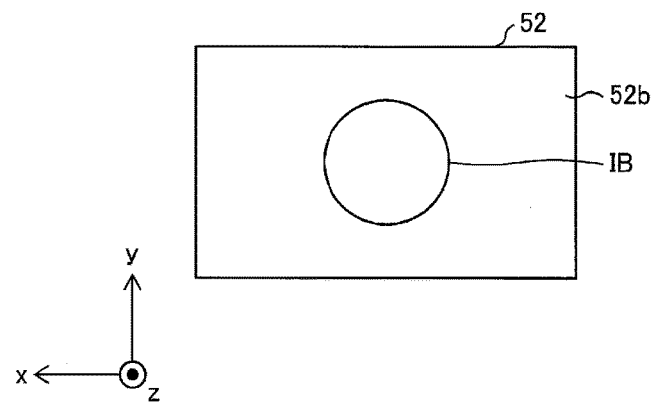
FIG. 7 is a view illustrating a condensing spot formed on a scattering member provided in the infrared projector illustrated in FIG. 6.

FIG. 7 is a view illustrating a condensing spot IB that is formed by the near-infrared laser light beam L20 (refer to FIG. 6) condensed on the scattering member 52. As illustrated in FIG. 7, the near-infrared laser light beam L20 condensed by the condenser lens 203 forms the condensing spot IB on the rear surface 52b of the scattering member 52. In the present embodiment, a shape of the condensing spot IB is a round shape whose diameter is 1.2 mm.

Figure 8:
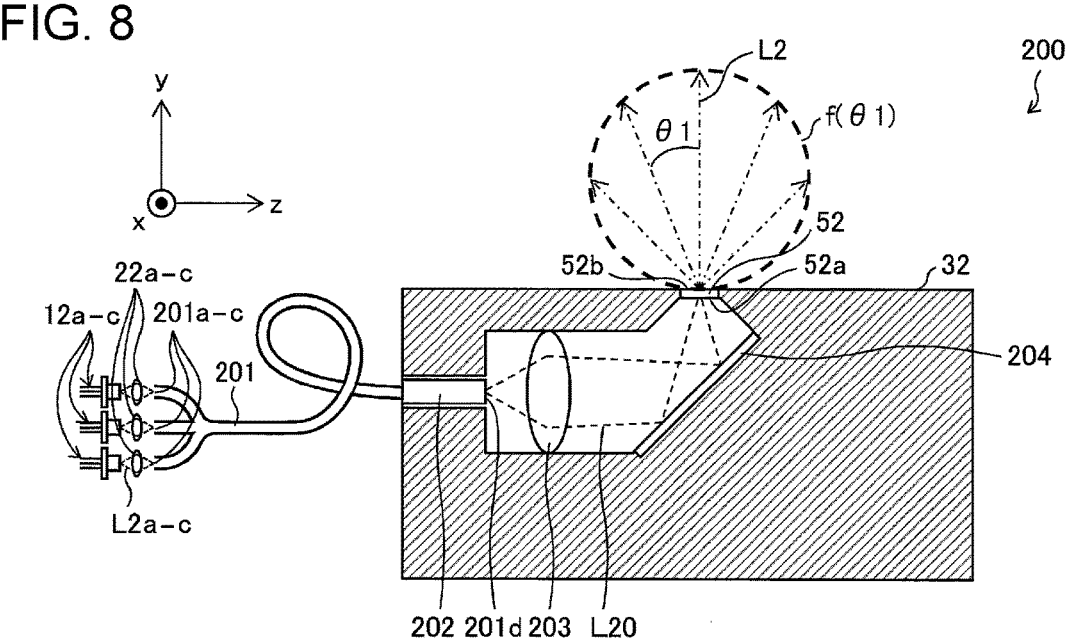
FIG. 8 is a view illustrating a state in which near-infrared laser light beams illustrated in FIG. 7 are scattered.

FIG. 8 is a view illustrating a state in which the near-infrared laser light beam scattered by the scattering member 52 is scattered. The near-infrared laser light beam L20 condensed on the front surface 52a of the scattering member 52 is isotropically scattered as the scattered light L21 to a side of the rear surface 52b by fine unevenness provided in at least one of the front surface 52a and the rear surface 52b. Intensity distribution of the scattered light L21 substantially obeys Lambert distribution.

Referring to FIG. 6 again here, the scattered light L21 scattered by the scattering member 52 enters the projecting member 62. The projecting member 62 projects the entered scattered light L21 as projected light L22.

(Configuration of Moving Mechanism 73)

Figure 9:
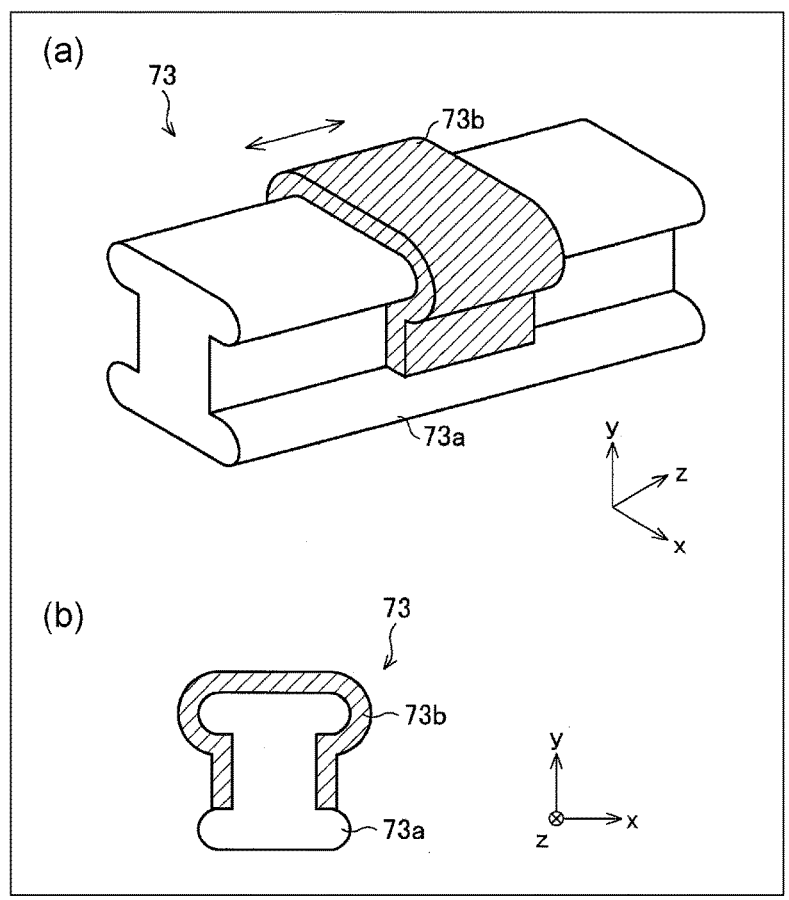
FIG. 9 is a view illustrating an example of a moving mechanism that moves a projecting member provided in the infrared projector according to Embodiment 2 of the invention, in which (a) is a perspective view and (b) is a front view.

FIG. 9 is a view illustrating an example of the moving mechanism 73 that moves the projecting member 62, in which (a) is a perspective view and (b) is a front view. As illustrated in (a) and (b) of FIG. 9, the moving mechanism 73 includes a guiding member 73a and a sliding member 73b.

The guiding member 73a is a member whose cross section is substantially I-shaped and is fixed to the housing 32. The sliding member 73b is a member that has, in the cross section thereof, a part substantially C-shaped and a linear part extending from an opening of the substantial C-shape. The linear part fits to a concave of the substantial I-shape of the guiding member 73a. The supporting member 205 (refer to FIG. 6) is fixed to the sliding member 73b.

The sliding member 73b is configured so as to be able to slide along the guiding member 73a. By sliding the sliding member 73b, it is possible to move the projecting member 62 that is supported by the supporting member 205 fixed to the sliding member 73b with respect to the scattering member 52 that is fixed to the housing 32.

A position of the projecting member 62 with respect to the scattering member 52 is adjusted so that spread of the projected light from the projecting member 62 becomes minimum.

(Effect of Infrared Projector 200)

In the infrared projector 200, a member that is transparent to infrared rays is used as the scattering member 52, and the front surface 52a serving as an entering surface of the near-infrared laser light beam L20 and the rear surface 52b serving as an emitting surface of the scattered light L21 that is scattered are opposed to each other.

At this time, the rear surface 52b of the scattering member 52 functions as a pseudo-light source that emits the scattered light L21 in which the plurality of near-infrared laser light beams L2a to L2c whose peak wavelengths are different are mixed.

Thus, a projection pattern of the infrared projector 200 is configured by the projected light from the single pseudo-light source, so that the infrared projector 200 is an infrared projector by which deviation of projection patterns of a plurality of near-infrared laser light beams is not caused in the projection patterns. Furthermore, in a case where wavelengths of a plurality of near-infrared light beams are different, the infrared projector 200 is an infrared projector by which unevenness of wavelengths is not caused in a projection pattern.

In the infrared projector 100, the scattering member 51 is not transparent to infrared rays, and an entering side and an emitting side of a near-infrared laser light beam coincide with each other. On the other hand, in the infrared projector 200, the scattering member 52 is transparent to infrared rays, and an entering side and an emitting side of a near-infrared laser light beam are opposed to each other, as described above. Either of the configurations of the infrared projector 100 and the infrared projector 200 is able to be used as a configuration of an infrared projector.

Embodiment 3

Another embodiment of the invention will be described as follows on the basis of FIG. 10 and FIG. 11. Note that, for convenience of description, the same reference signs are assigned to members having the same functions as those of the members described in the above-described embodiments, and description thereof is omitted.

In an infrared projector 300 according to the present embodiment, an emitting end 53b of a light guiding member 53 that is a rod lens having a rectangular cross section functions as a pseudo-light source of a near-infrared laser light beam having a plurality of peak wavelengths.

(Outline of Infrared Projector 300)

Figure 10:
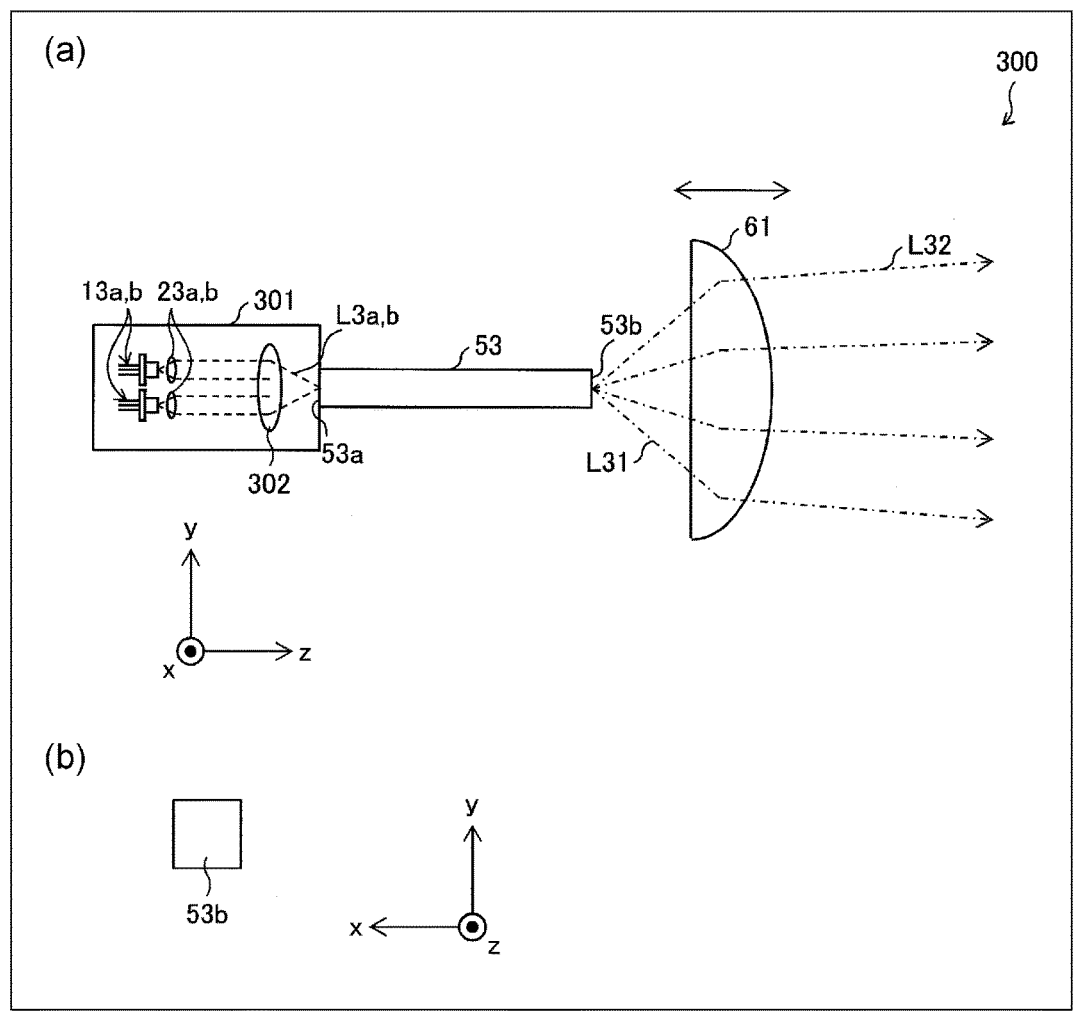
FIG. 10 (a) is a schematic view of an infrared projector according to Embodiment 3 of the invention, and (b) is a view illustrating a shape of an emitting end of a light guiding member provided in the infrared projector.

(a) of FIG. 10 is a view illustrating an outline of the infrared projector 300. As illustrated in (a) of FIG. 10, the infrared projector 300 is provided with a light source 301, the light guiding member 53, and the projecting member 61. The light source 301 is provided with two infrared semiconductor laser elements 13a and 13b, two condenser lenses 23a and 23b, and a condenser lens 302.

The infrared semiconductor laser elements 13a and 13b are laser light sources which emit near-infrared laser light beams L3a and L3b, respectively. Each of the infrared semiconductor laser elements 13a and 13b is attached to a heat sink (not illustrated) for heat radiation, and connected to a power source circuit (not illustrated) for drive.

In the present embodiment, an output of each of the infrared semiconductor laser elements 13a and 13b is 1 W. Moreover, in the present embodiment, peak wavelengths of the near-infrared laser light beams L3a and L3b are 790 nm and 810 nm, respectively.

The condenser lenses 23a and 23b are members that condense the near-infrared laser light beams L3a and L3b. In the present embodiment, the condenser lenses 23a and 23b are convex lenses made of glass.

The condenser lens 302 is a member that further condenses the near-infrared laser light beams L3a and L3b condensed by the condenser lenses 23a and 23b. In the present embodiment, the condenser lens 302 is a convex lens made of glass.

The light guiding member 53 is a member that guides the near-infrared laser light beams L3a and L3b. The light guiding member 53 includes an entering end (one end) 53a which the near-infrared laser light beams L3a and L3b enter and the emitting end (the other end) 53b from which scattered light L31 in which the near-infrared laser light beams L3a and L3b are mixed is emitted.

In the present embodiment, the light guiding member 53 is a rod lens. More specifically, the light guiding member 53 is a member an inside of which is filled with glass and the cross section of which is rectangular. The near-infrared laser light beams L3a and L3b are guided while being reflected by an inner wall of the light guiding member 53 due to total reflection caused by a refractive index difference between glass and air. Additionally, a material which is transparent to wavelengths of the near-infrared laser light beams L3a and L3b, such as resin, sapphire, crystal, may be used as a material of the light guiding member 53.

Moreover, a light guiding member which is surrounded by a wall made of a thin material that is transparent to the wavelengths of the near-infrared laser light beams L3a and L3b and which is hollow may be used instead of the light guiding member 53. In this case, similarly to the light guiding member 53, glass, resin, sapphire, crystal, or the like may be used as the transparent thin material. Further, a light guiding member which is surrounded by a wall made of a material having high reflectance with respect to the near-infrared laser light beams L3a and L3b and which is hollow may be used.

(Operation of Infrared Projector 300)

In the infrared projector 300, the near-infrared laser light beams L3a and L3b are caused to enter the entering end 53a of the light guiding member 53 and the scattered light L31 emitted from the emitting end 53b is projected by the projecting member 61. An operation of the infrared projector 300 will be described below.

As illustrated in (a) of FIG. 10, the infrared semiconductor laser elements 13a and 13b emit the near-infrared laser light beams L3a and L3b toward the condenser lens 302. The near-infrared laser light beams L3a and L3b enter the condenser lens 302 via the condenser lenses 23a and 23b. The near-infrared laser light beams L3a and L3b which have entered the condenser lens 302 are condensed on the entering end 53a of the light guiding member 53, and enter the light guiding member 53.

(b) of FIG. 10 is a view illustrating a shape of the emitting end 53b of the light guiding member 53. In the light guiding member 53, the near-infrared laser light beams L1a and L3b entered from the entering end 53a are mixed, and emitted from the emitting end 53b as the scattered light L31.

Figure 11:
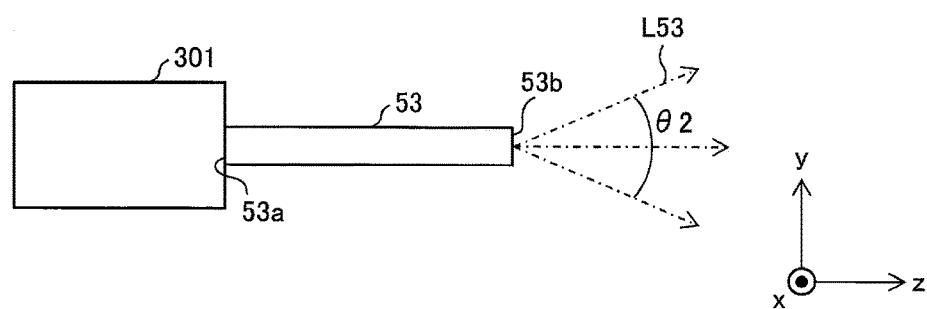
FIG. 11 is a view illustrating a state in which near-infrared laser light beams are scattered at the emitting end of the light guiding member illustrated in (b) of FIG. 10.

FIG. 11 is a view illustrating a state in which the scattered light L31 is scattered. As illustrated in FIG. 11, the scattered light L31 is radiated in a range of a predetermined radiation angle $\theta 2$. Here, the radiation angle $\theta 2$ is a spread angle of the scattered light L31 on a plane including the z-axis. In the present embodiment, $\theta 2 = 60°$ is provided.

Referring to (a) of FIG. 10 again here, the scattered light L31 radiated from the emitting end 53b of the light guiding member 53 enters the projecting member 61. The projecting member 61 projects the entered scattered light L31 as projected light L32.

(Effect of Infrared Projector 300)

In the infrared projector 300, not a scattering member that isotropically scatters a near-infrared laser light beam but the emitting end 53b of the light guiding member 53 functions as a pseudo-light source. Also with such a configuration, it is possible to realize an infrared projector in which a plurality of near-infrared laser light beams are mixed and by which deviation of projection patterns of the plurality of near-infrared laser light beams is not caused in the projection patterns. Furthermore, in a case where wavelengths of a plurality of near-infrared light beams are different, the infrared projector 300 is an infrared projector by which unevenness of wavelengths is not caused in a projection pattern.

Embodiment 4

Another embodiment of the invention will be described as follows on the basis of FIG. 12 and FIG. 13. Note that, for convenience of description, the same reference signs are assigned to members having the same functions as those of the members described in the above-described embodiments, and description thereof is omitted.

In an infrared projector 400 according to the present embodiment, an emitting end 54b of a light guiding member 54 that is a multimode fiber functions as a pseudo-light source of a near-infrared laser light beam having a plurality of peak wavelengths. Moreover, a projecting member 63 that is a parabolic mirror is provided as a projecting member.

(Outline of Infrared Projector 400)

Figure 12:
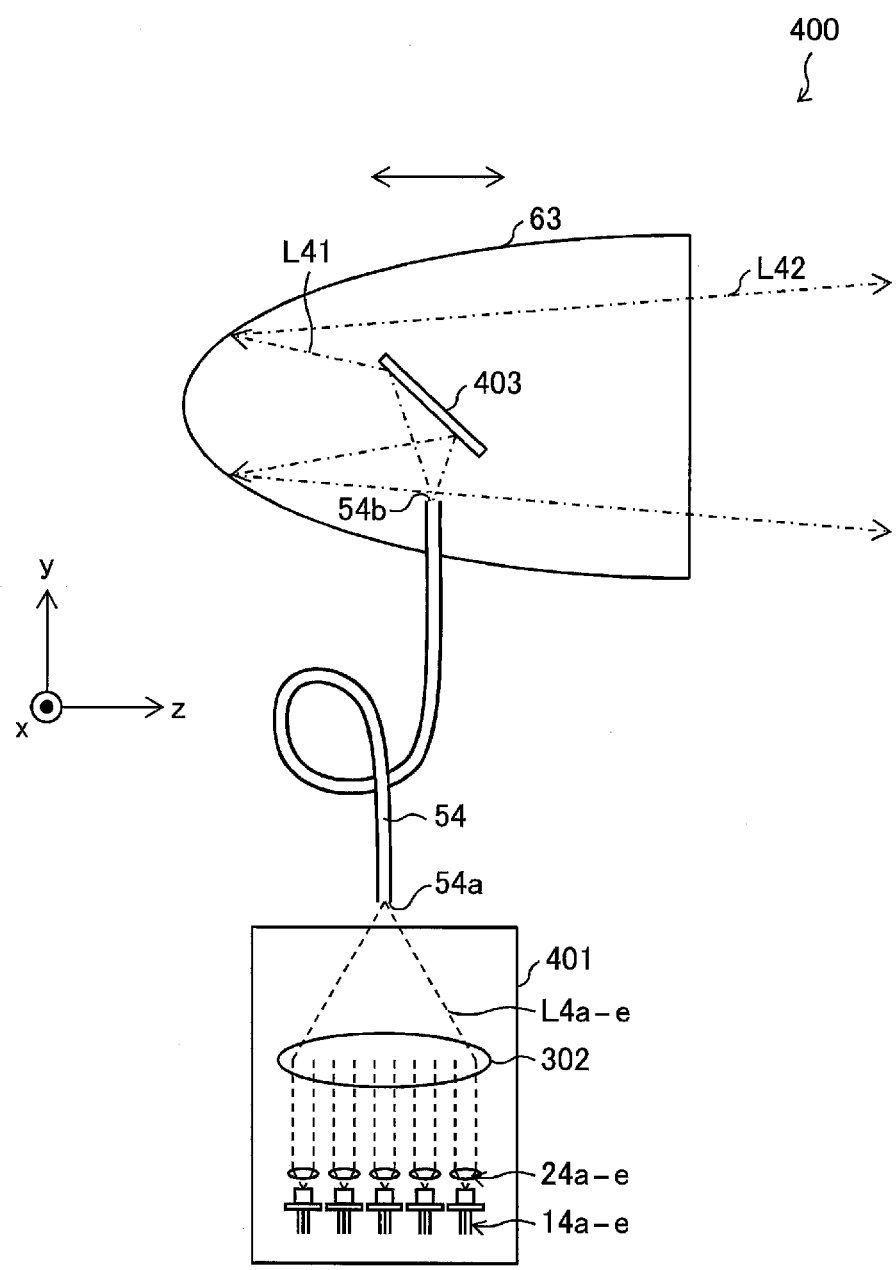
FIG. 12 is a schematic view of an infrared projector according to Embodiment 4 of the invention.

FIG. 12 is a view illustrating an outline of the infrared projector 400 according to the present embodiment. As illustrated in FIG. 12, the infrared projector 400 is provided with a light source 401, the light guiding member 54, a folding mirror 403, and the projecting member 63. The light source 401 is provided with five infrared semiconductor laser elements 14a, 14b, 14c, 14d, and 14e, five condenser lenses 24a, 24b, 24c, 24d, and 24e, and the condenser lens 302.

The infrared semiconductor laser elements 14a to 14e are laser light sources which emit near-infrared laser light beams L4a to L4e, respectively. Each of the infrared semiconductor laser elements 14a to 14e is attached to a heat sink (not illustrated) for heat radiation, and connected to a power source circuit (not illustrated) for drive.

In the present embodiment, an output of each of the infrared semiconductor laser elements 14a to 14e is 0.5 W. Moreover, in the present embodiment, peak wavelengths of the near-infrared laser light beams L4a to L4e are 780 nm, 790 nm, 800 nm, 810 nm, and 820 nm, respectively.

The condenser lenses 24a to 24e are members that condense the near-infrared laser light beams L4a to L4e. In the present embodiment, the condenser lenses 24a to 24e are convex lenses made of glass.

The light guiding member 54 is a member that guides the near-infrared laser light beams L4a to L4e in a mixed manner. The light guiding member 54 includes an entering end (one end) 54a which the near-infrared laser light beams L4a to L4e enter and the emitting end (the other end) 54b from which scattered light L41 in which the near-infrared laser light beams L4a to L4e are mixed is emitted. In the present embodiment, the light guiding member 54 is a multimode fiber. More specifically, the light guiding member 54 is a multimode fiber having a round-shaped core a diameter of a cross section of which is 800 μm.

A material of the multimode fiber is able to be selected from glass, quartz, resin, and the like. In addition, the material of the multimode fiber may be a photonic crystal fiber. Furthermore, a shape of the core is not limited to the round shape, and may be any shape such as a rectangular shape.

The folding mirror 403 is a member that folds the scattered light L41 which is emitted from the emitting end 54b of the light guiding member 54 and in which the near-infrared laser light beams L4a to L4e are mixed.

The projecting member 63 is a member that projects the scattered light L41 folded by the folding mirror 403 to an outside. In the present embodiment, the projecting member 63 is a parabolic mirror, that is, a concave mirror having a shape of a paraboloid of revolution. Moreover, the projecting member 63 may be a concave mirror having any curved surface such as a free curved surface.

(Operation of Infrared Projector 400)

In the infrared projector 400, the near-infrared laser light beams L4a to L4e are caused to enter the entering end 54a of the light guiding member 54 and the scattered light L41 emitted from the emitting end 54b of the light guiding member 54 is folded by the folding mirror 403 and projected by the projecting member 63. An operation of the infrared projector 400 will be described below.

As illustrated in FIG. 12, the infrared semiconductor laser elements 14a to 14e emit the near-infrared laser light beams L4a to L4e toward the entering end 54a of the light guiding member 54. The near-infrared laser light beams L4a to L4e go through the condenser lenses 24a to 24e and the condenser lens 302 and come together at the entering end 54a of the light guiding member 54 to enter the light guiding member 54.

The near-infrared laser light beams L4a to L4e entered the light guiding member 54 are mixed in an inside of the light guiding member 54. The mixed near-infrared laser light beams L4a to L4e are emitted from the emitting end 54b as the scattered light L41, for example, at NA (Numerical Aperture)=0.2.

The scattered light L41 is folded by the folding mirror 403 toward the projecting member 63. The projecting member 63 projects the scattered light L41 folded by the folding mirror 403 as projected light L42.

(Configuration of Moving Mechanism 74)

Figure 13:
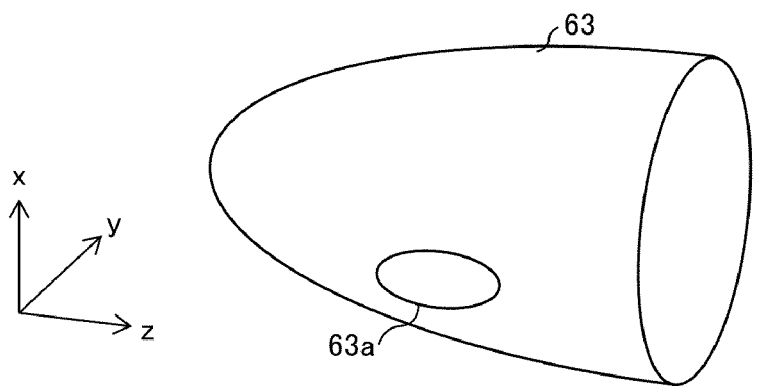
FIG. 13 (a) is a perspective view of a projecting member provided in the infrared projector illustrated in FIG. 12, and (b) is a view illustrating an example of a moving mechanism that moves a folding mirror provided in the infrared projector illustrated in FIG. 12.
Figure 13:
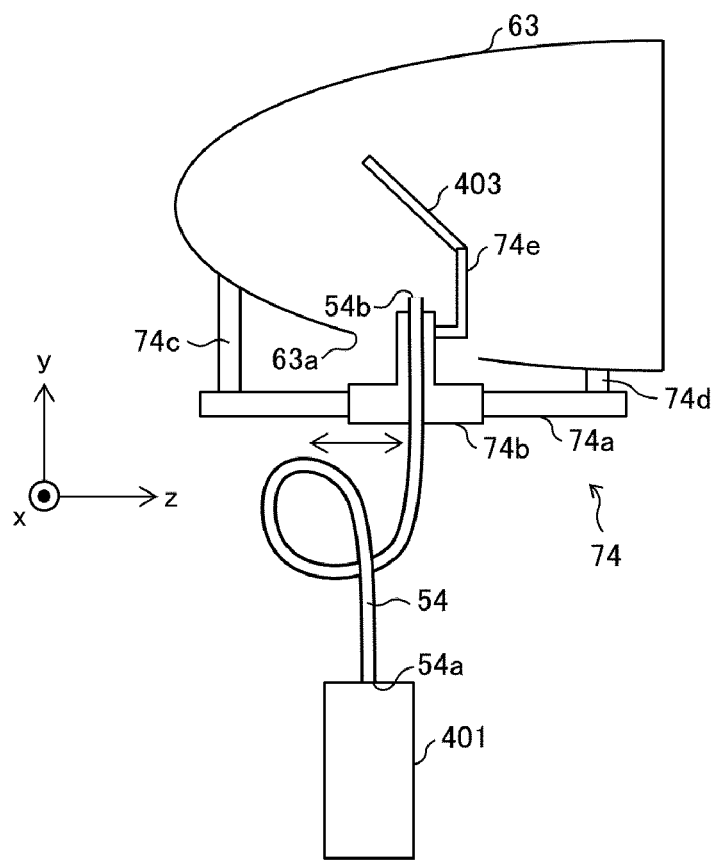

(a) of FIG. 13 is a perspective view of the projecting member 63. As illustrated in (a) of FIG. 13, the projecting member 63 is provided with a notch 63a. The notch 63a has a predetermined length in the z direction.

(b) of FIG. 13 is a view illustrating an example of a moving mechanism 74 that moves the folding mirror 403 and the emitting end 54b of the light guiding member 54 in the z direction. As illustrated in (b) of FIG. 13, the moving mechanism 74 is provided with a guiding member 74a, a sliding member 74b, projecting member supporting members 74c and 74d, and a folding mirror supporting member 74e.

The guiding member 74a is a bar-shaped member that is arranged parallel to the z-axis. The sliding member 74b is a member attached to the guiding member 74a so as to be able to slide. The emitting end 54b of the light guiding member 54 is fixed to the sliding member 74b.

The projecting member supporting members 74c and 74d are members that support the projecting member 63. The projecting member supporting members 74c and 74d are fixed to the guiding member 74a.

The folding mirror supporting member 74e is a member that supports the folding mirror 403. The folding mirror supporting member 74e is attached to the sliding member 74b. Accordingly, a position of the folding mirror 403 with respect to the emitting end 54b of the light guiding member 54 is fixed.

By sliding the sliding member 74b on the guiding member 74a, it is possible to move the folding mirror 403 and the emitting end 54b of the light guiding member 54 with respect to the projecting member 63. A range in which the sliding member 74b is able to slide is determined in accordance with the length of the notch 63a in the z direction.

A position of the folding mirror 403 with respect to the projecting member 63 is adjusted so that spread of the projected light by the projecting member 63 becomes minimum.

(Effect of Infrared Projector 400)

In the infrared projector 400, the emitting end 54b of the light guiding member 54 that is a multimode fiber functions as a pseudo-light source of the scattered light L41. Since, in the infrared projector 400, the plurality of near-infrared laser light beams L4a to L4e having different peak wavelengths are mixed in a process of being guided in the inside of the light guiding member 54, the infrared projector 400 is an infrared projector by which deviation of projection patterns of the plurality of near-infrared laser light beams is not caused in the projection patterns. Furthermore, in a case where wavelengths of a plurality of near-infrared light beams are different, the infrared projector 400 is an infrared projector by which unevenness of wavelengths is not caused in a projection pattern.

Embodiment 5

Another embodiment of the invention will be described as follows on the basis of FIG. 14 to FIG. 16. Note that, for convenience of description, the same reference signs are assigned to members having the same functions as those of the members described in the above-described embodiments, and description thereof is omitted.

In an infrared projector 500 according to the present embodiment, a front surface 55a of a scattering member 55 which is formed of ceramic and is dome-shaped functions as a pseudo-light source of scattered light L51 having a plurality of peak wavelengths.

(Outline of Infrared Projector 500)

Figure 14:
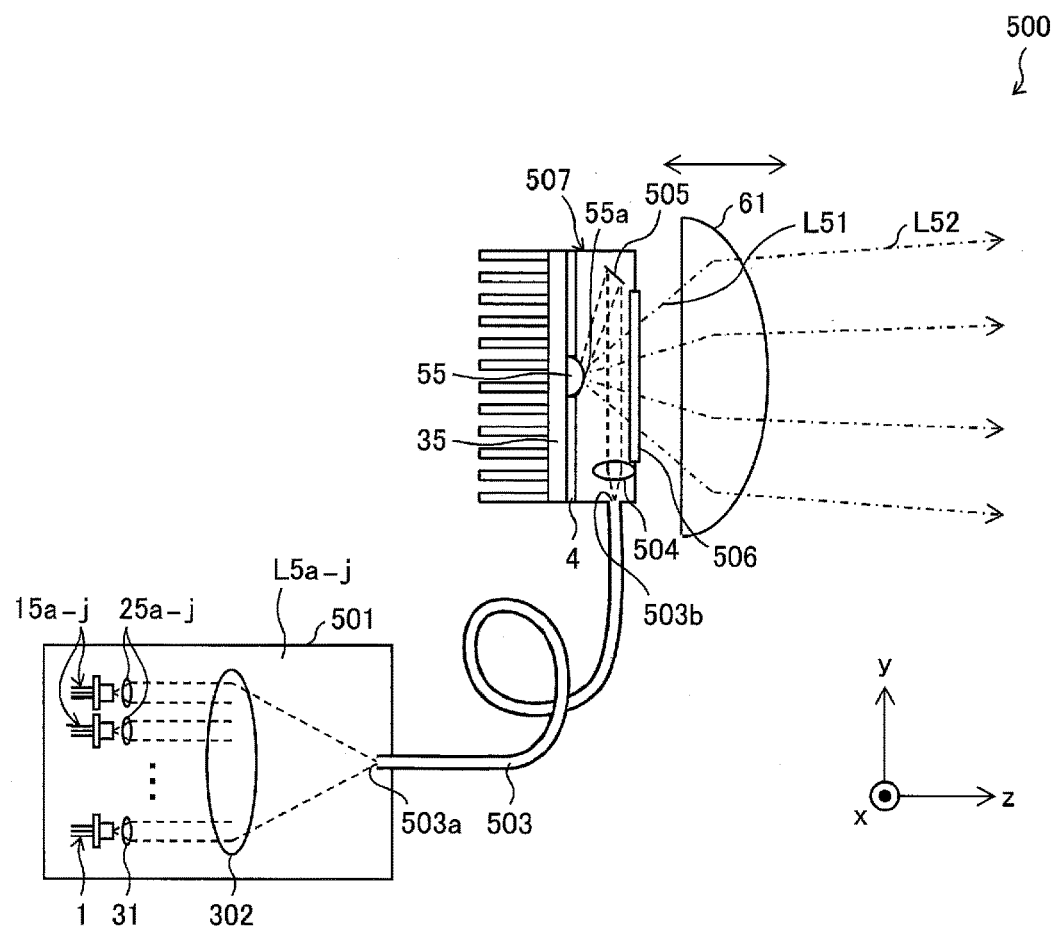
FIG. 14 is a schematic view of an infrared projector according to Embodiment 5 of the invention.

FIG. 14 is a view illustrating an outline of the infrared projector 500. As illustrated in FIG. 14, the infrared projector 500 is provided with a light source 501, an optical transmission path 503, a lens 504, a reflecting mirror 505, the scattering member 55, the light absorbing material 4, a supporting base 35, a window member 506, a frame member 507, and the projecting member 61. The light source 501 is provided with ten infrared semiconductor laser elements 15a, 15b, 15c, 15d, 15e, 15f, 15g, 15h, 15i, and 15j, ten condenser lenses 25a, 25b, 25c, 25d, 25e, 25f, 25g, 25h, 25i, and 25j, and the condenser lens 302.

The infrared semiconductor laser elements 15a to 15j are laser light sources which emit near-infrared laser light beams L5a to L5j, respectively. Each of the infrared semiconductor laser elements 15a to 15j is attached to a heat sink (not illustrated) for heat radiation, and connected to a power source circuit (not illustrated) for drive.

In the present embodiment, an output of each of the infrared semiconductor laser elements 15a to 15j is 0.5 W. Moreover, in the present embodiment, peak wavelengths of the near-infrared laser light beams L5a to L5j are 810 nm to 900 nm at 10 nm intervals.

The condenser lenses 25a to 25j are members that condense the near-infrared laser light beams L5a to L5j. In the present embodiment, the condenser lenses 25a to 25j are convex lenses made of glass.

The optical transmission path 503 is a member that transmits the near-infrared laser light beams L5a to L5j in a mixed manner. The optical transmission path 503 includes an entering end 503a and an emitting end 503b. In the present embodiment, the optical transmission path 503 is a multimode fiber having a round-shaped core.

The lens 504 is a convex lens that condenses a near-infrared laser light beam L50 which is emitted from the emitting end 503b of the optical transmission path 503 and in which the near-infrared laser light beams L5a to L5j are mixed.

The reflecting mirror 505 is a member that reflects the near-infrared laser light beam L50. The reflecting mirror 505 may be a plate covered with metal such as aluminum or a mirror made of metal. Alternatively, the reflecting mirror 505 may be a multilayer-film reflecting mirror covered with a dielectric.

The scattering member 55 is a member that receives the near-infrared laser light beam L50 reflected by the reflecting mirror 505 and scatters the received near-infrared laser light beam L50 as the scattered light L51. The scattering member 55 includes the front surface 55a which is a surface that the near-infrared laser light beam L50 enters. In the present embodiment, the scattering member 55 is a member that has fine unevenness on the front surface 55a and is in domeshaped and formed of ceramic.

More specifically, the scattering member 55 is a member made of ceramic, in which roughness of the front surface 55a satisfies Ra=1 μm. Alumina, barium sulfate, or the like is able to be used as a material of the scattering member 55, for example. Moreover, the front surface 55a of the scattering member 55 is a curved surface a center part of which protrudes in the positive direction of the z direction compared with an outer peripheral part.

The supporting base 35 is a base that supports the light absorbing material 4 and the scattering member 55. In the present embodiment, the supporting base 35 is made of aluminum. Note that, the supporting base 35 may be formed of another material, for example, such as another metal or highly heat-conductive ceramic. Moreover, in the present embodiment, in the supporting base 35, a surface opposite to a surface supporting the scattering member 55 is processed so as to be a heat radiation fin so that heat generated when the near-infrared laser light beam L50 enters the scattering member 55 is efficiently radiated.

The window member 506 is a window which is provided between the scattering member 55 and the projecting member 61 and through which light passes. In the present embodiment, the window member 506 is a plate-shaped glass. The frame member 507 is a frame that supports the window member 506.

(Operation of Infrared Projector 500)

In the infrared projector 500, the near-infrared laser light beam L50 is caused to enter the front surface 55a of the scattering member 55 and the scattered light L51 scattered to a side of the front surface 55a of the scattering member 55 is projected by the projecting member 61. An operation of the infrared projector 500 will be described below.

As illustrated in FIG. 14, the infrared semiconductor laser elements 15a to 15j emit the near-infrared laser light beams L5a to L5j toward the entering end 503a of the optical transmission path 503. The near-infrared laser light beams L5a to L5j go through the condenser lenses 25a to 25j and the condenser lens 302 and come together at the entering end 503a of the optical transmission path 503 to enter the optical transmission path 503. The near-infrared laser light beams L5a to L5j entered the optical transmission path 503 are mixed in an inside of the optical transmission path 503, and emitted from the emitting end 503b of the optical transmission path 503 as the near-infrared laser light beam L50. Spread of the emitted near-infrared laser light beam L50 is suppressed by the lens 504, and the emitted near-infrared laser light beam L50 is reflected by the reflecting mirror 505 toward the scattering member 55.

Figure 15:
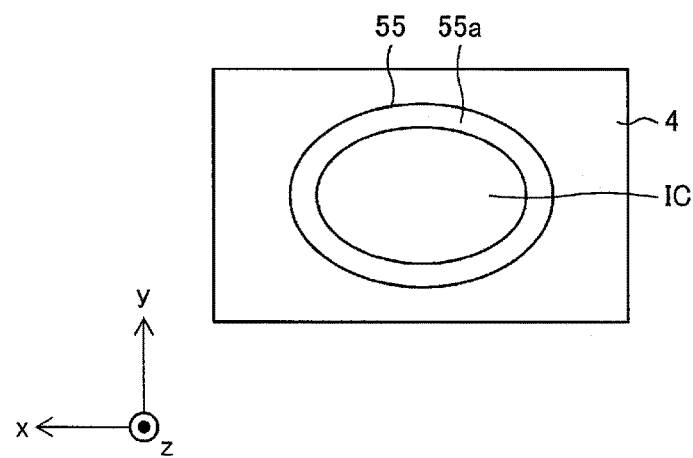
FIG. 15 is a view illustrating a condensing spot formed on a scattering member provided in the infrared projector illustrated in FIG. 14.

FIG. 15 is a view illustrating a condensing spot IC formed on the front surface 55a of the scattering member 55 by the near-infrared laser light beam L50 (refer to FIG. 14) entered the scattering member 55. As illustrated in FIG. 15, the near-infrared laser light beam L50 entered the scattering member 55 forms the condensing spot IC on the front surface 55a. In the present embodiment, a shape of the condensing spot IC is an ellipse.

Figure 16:
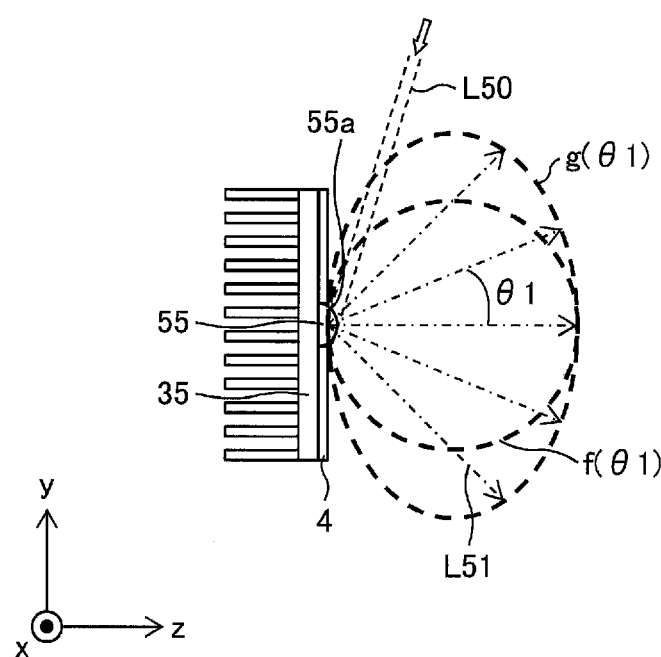
FIG. 16 is a view illustrating a state in which near-infrared laser light beams are scattered by the scattering member provided in the infrared projector, which is illustrated in FIG. 15.

FIG. 16 is a view illustrating a state in which the scattered light L51 is scattered by the scattering member 55. As illustrated in FIG. 16, the near-infrared laser light beam L50 entered the front surface 55a of the scattering member 55 is isotropically scattered to the side of the front surface 55a as the scattered light L51 as indicated with $g(\theta 1)$.

In FIG. 16, intensity at an angle $\theta 1$ in a case where intensity distribution of a scattered near-infrared laser light beam obeys Lambert distribution is indicated with $f(\theta 1)$. On the other hand, intensity of the scattered light L51 scattered by the scattering member 55 becomes greater than $f(\theta 1)$ in a region of $\theta 1 \neq 0°$, as indicated with $g(\theta 1)$ in FIG. 16.

Specifically, while $f(\theta 1)$ is a round shape, $g(\theta 1)$ is an ellipse. In a case where intensity of the two types of scattered light is the same when $\theta 1=0°$ is satisfied, a difference between $g(\theta 1)$ and $f(\theta 1)$ becomes particularly great when $\theta 1=45°$ is satisfied. Moreover, when $\theta 1 \approx 90°$ is satisfied, while $f(\theta 1) \approx 0$ is provided, $g(\theta 1)$ has intensity to some extent.

That is, the scattered light L51 scattered by the scattering member 55 is distributed over a wider angle than Lambert distribution.

Referring to FIG. 14 again here, the projecting member 61 projects the scattered light L51 scattered by the scattering member 55 as projected light L52.

(Effect of Infrared Projector 500)

The infrared projector according to the present embodiment is an infrared projector by which deviation of projection patterns of a plurality of near-infrared laser light beams is not caused in the projection patterns. Furthermore, in a case where wavelengths of a plurality of near-infrared light beams are different, the infrared projector 500 is an infrared projector by which unevenness of wavelengths is not caused in a projection pattern.

In the infrared projector 500 according to the present embodiment, the condensing spot IC formed on the front surface 55a of the scattering member 55 which is the dome-shaped member made of ceramic functions as a pseudo-light source of the scattered light L51.

The intensity distribution of the scattered light L51 scattered by the scattering member 55 is distributed over a wider angle than Lambert distribution. Moreover, a shape of the scattering member is not limited to the dome shape as the scattering member 55, and may be changed into any of a corn, a polygonal pyramid such as a triangular pyramid or a quadrangular pyramid, a truncated shape such as a truncated corn or a truncated quadrangular pyramid, or modification of them, for example. By changing the shape of the scattering member, it is possible to change the intensity distribution of the near-infrared laser light beam scattered by the scattering member into any distribution.

Embodiment 6

Another embodiment of the invention will be described as follows on the basis of FIG. 17 and FIG. 18. Note that, for convenience of description, the same reference signs are assigned to members having the same functions as those of the members described in the above-described embodiments, and description thereof is omitted.

In an infrared projector 600 according to the present embodiment, an emitting surface 56b of a light guiding member 56 functions as a pseudo-light source of scattered light L61 having a plurality of peak wavelengths.

(Outline of Infrared Projector 600)

Figure 17:
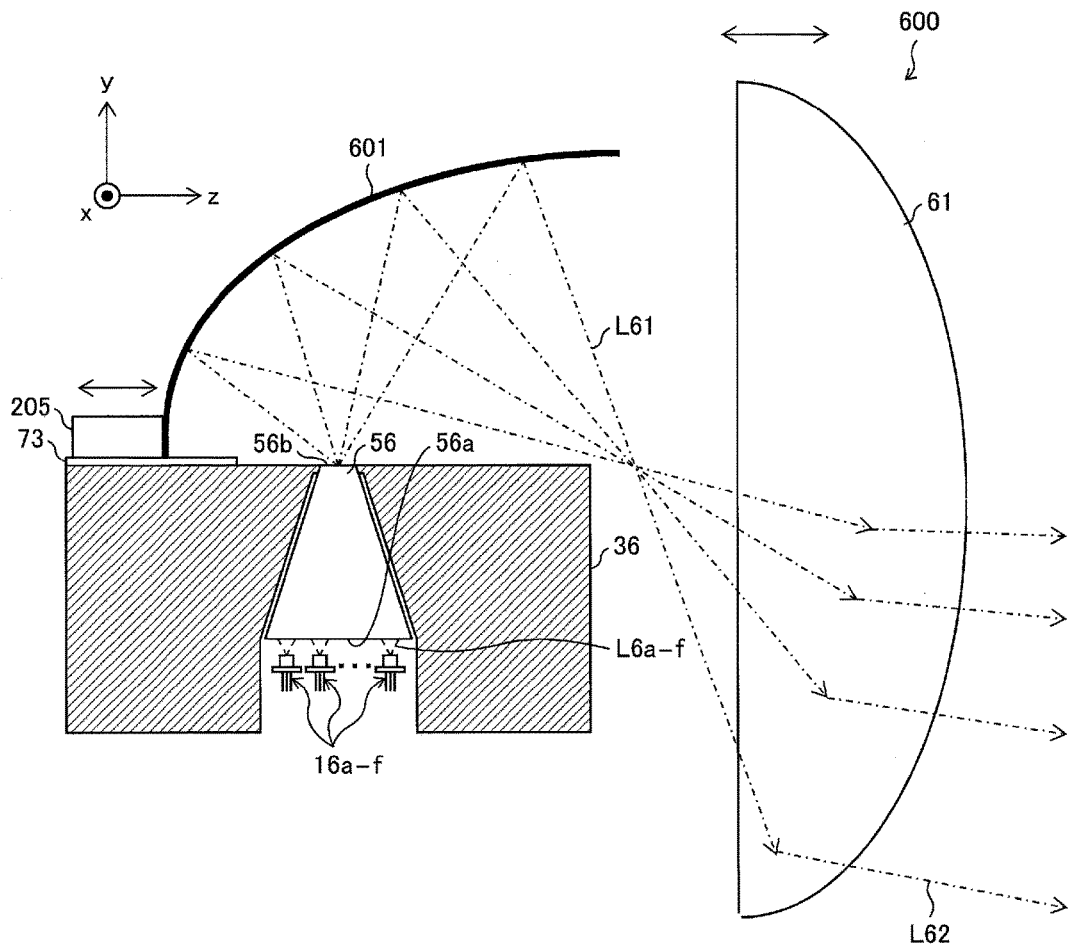
FIG. 17 is a schematic view of an infrared projector according to Embodiment 6 of the invention.
Figure 18:
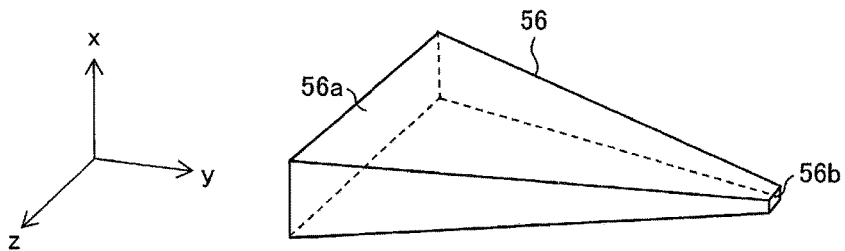
FIG. 18 is a view illustrating a light guiding member provided in the infrared projector illustrated in FIG. 17.

FIG. 17 is a view illustrating an outline of the infrared projector 600. As illustrated in FIG. 17, the infrared projector 600 is provided with six infrared semiconductor laser elements 16a, 16b, 16c, 16d, 16e, and 16f, the light guiding member 56, a reflecting mirror 601, the projecting member 61, a housing 36, the supporting member 205, and the moving mechanism 73.

The infrared semiconductor laser elements 16a to 16f are laser light sources which emit near-infrared laser light beams L6a to L6f, respectively. Each of the infrared semiconductor laser elements 16a to 16f is attached to a heat sink (not illustrated) for heat radiation, and connected to a power source circuit (not illustrated) for drive.

In the present embodiment, an output of each of the infrared semiconductor laser elements 16a to 16f is 0.5 W. Moreover, in the present embodiment, peak wavelengths of the near-infrared laser light beams L6a to L6f are 780 nm, 800 nm, 820 nm, 840 nm, 860 nm, and 880 nm, respectively.

The light guiding member 56 is a member that guides the near-infrared laser light beams L6a to L6f. FIG. 18 is a view illustrating the light guiding member 56. As illustrated in FIG. 18, the light guiding member 56 includes an entering surface (one end) 56a which the near-infrared laser light beams L6a to L6f enter and the emitting surface (the other end) 56b from which the scattered light L61 in which the near-infrared laser light beams L6a to L6f are mixed is emitted.

In the present embodiment, the light guiding member 56 is formed so that an area of the entering surface 56a is larger than an area of the emitting surface 56b. Moreover, a material of the light guiding member 56 may be selected from glass, quartz, sapphire, resin, and the like.

The reflecting mirror 601 is a member that reflects a near-infrared laser light beam. In the present embodiment, the reflecting mirror 601 is an elliptic mirror.

The housing 36 is a member that accommodates the infrared semiconductor laser elements 16a to 16f in an inside thereof and holds the light guiding member 56 by side surfaces thereof. In the present embodiment, a material of the housing 36 is metal.

(Operation of Infrared Projector 600)

In the infrared projector 600, the near-infrared laser light beams L6a to L6f are caused to enter the entering surface 56a of the light guiding member 56 and the scattered light L61 scattered from the emitting surface 56b of the light guiding member 56 is projected by the reflecting mirror 601 and the projecting member 61. An operation of the infrared projector 600 will be described below.

As illustrated in FIG. 17, the infrared semiconductor laser elements 16a to 16f emit the near-infrared laser light beams L6a to L6f toward the entering surface 56a of the light guiding member 56. The near-infrared laser light beams L6a to L6f entered the light guiding member 56 are mixed in an inside of the light guiding member 56, and emitted from the emitting surface 56b as the scattered light L61. The scattered light L61 is reflected by the reflecting mirror 601 toward the projecting member 61. The projecting member 61 projects the scattered light L61 from the reflecting mirror 601 as projected light L62.

A position of the reflecting mirror 601 with respect to the light guiding member 56 and a position of the projecting member 61 with respect to the reflecting mirror 601 are adjusted so that spread of the projected light by the projecting member 61 becomes minimum. Specifically, the adjustment is performed so that a z coordinate of one focal point of two focal points included by the reflecting mirror 601 that is an elliptic mirror coincides with a z coordinate of the center of the emitting surface 56b of the light guiding member 56, and a z coordinate of the other focal point coincides with a z coordinate of a focal point of the projecting member 61.

The infrared projector according to the present embodiment is an infrared projector by which deviation of projection patterns of a plurality of near-infrared laser light beams is not caused in the projection patterns. Furthermore, in a case where wavelengths of a plurality of near-infrared light beams are different, the infrared projector 600 is an infrared projector by which unevenness of wavelengths is not caused in a projection pattern.

In the infrared projector 600, the emitting surface 56b of the light guiding member 56 that is a tapered light guiding member functions as a pseudo-light source of the scattered light L61.

Embodiment 7

Another embodiment of the invention will be described as follows on the basis of FIG. 19. Note that, for convenience of description, the same reference signs are assigned to members having the same functions as those of the members described in the above-described embodiments, and description thereof is omitted.

Figure 19:
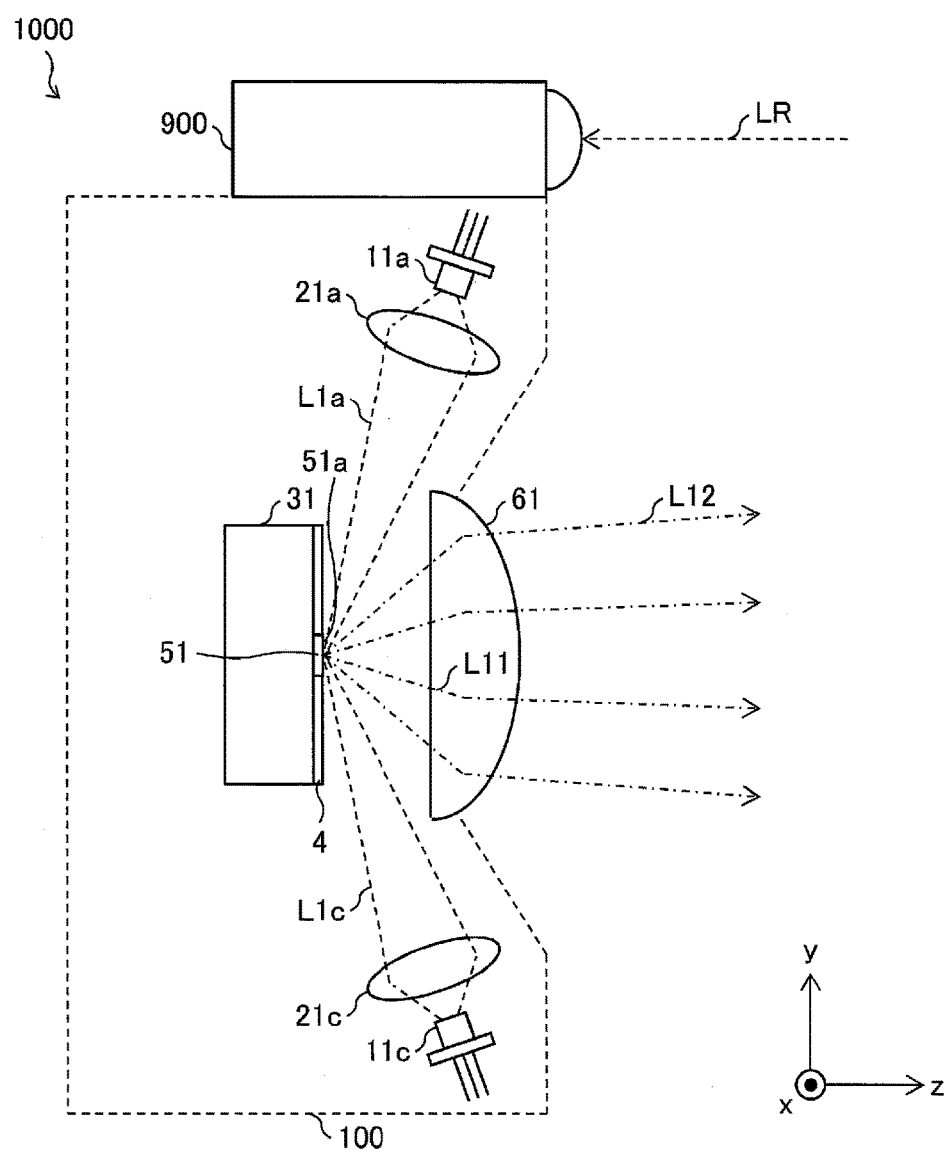
FIG. 19 is a schematic view of an infrared observation system according to Embodiment 7 of the invention.

FIG. 19 is a view illustrating an outline of an infrared observation system 1000 according to the present embodiment. As illustrated in FIG. 19, the infrared observation system 1000 is provided with the infrared projector 100 and a camera device 900 that captures an image formed by infrared rays projected from the infrared projector 100. Note that, a lens structure, an inner structure such as an image sensor, wirings, and the like of the camera device 900 are omitted.

In a case of observing an observation target by using the infrared observation system 1000, the infrared projector 100 projects, toward an outside, the projected light L12 in which the near-infrared laser light beams L1a to L1d whose peak wavelengths are different are mixed. The camera device 900 captures an image formed by a near-infrared laser light beam LR reflected by the aforementioned observation target.

As described above, the infrared projector 100 is an infrared projector by which deviation of projection patterns of a plurality of near-infrared laser light beams is not caused in the projection patterns. Furthermore, in a case where wavelengths of a plurality of near-infrared light beams are different, the infrared projector 100 is an infrared projector by which unevenness of wavelengths is not caused in a projection pattern. Thus, in the infrared observation system 1000, by the camera device 900, it is possible to observe an infrared image in which deviation of images of respective wavelengths, which is caused by unevenness of the wavelengths, is reduced.

Moreover, the infrared observation system may be provided any of the infrared projectors 200 to 600 instead of the infrared projector 100.

Note that, in the scattering member, a great amount of heat is generated when a near-infrared laser light beam is condensed. Accordingly, it is preferable that the scattering member is a member that has high heat conductivity and is not transparent to infrared rays and is configured so that an entering side and an emitting side of a near-infrared laser light beam coincide with each other. With such a configuration, it is possible to provide a mechanism which facilitates heat radiation of the scattering member, for example, such as a heat radiation fin on a surface of the scattering member, which is opposite to the entering side and the emitting side of the near-infrared laser light beam.

CONCLUSION

An infrared projector (100) according to an aspect 1 of the invention includes: a plurality of laser light sources (infrared semiconductor laser elements 11a, 11b, 11c, and 11d) that emit near-infrared laser light beams (L1a, L1b, L1c, and L1d); a scattering member (51) that receives the plurality of near-infrared laser light beams emitted from the plurality of laser light sources and scatters the received near-infrared laser light beams; and a projecting member (61) that projects the near-infrared laser light beams scattered by the scattering member.

With the aforementioned configuration, each of the plurality of laser light sources provided in the infrared projector emits each of the near-infrared laser light beams. The scattering member receives the plurality of near-infrared laser light beams emitted from the plurality of laser light sources and scatters the near-infrared laser light beams (L11). The projecting member projects the near-infrared laser light beams scattered by the scattering member (L12).

At this time, the scattering member scatters a near-infrared laser light beam in which the plurality of near-infrared laser light beams are mixed. That is, the scattering member functions as a single pseudo-light source that emits the mixed near-infrared laser light beams. Accordingly, an effect that an infrared projector by which unevenness of wavelengths in a projection pattern is reduced is able to be provided is achieved.

In an infrared projector according to an aspect 2 of the invention, it is preferable that, in the aspect 1, the projecting member forms an image of a condensing spot of the near-infrared laser light beams, which is formed on the scattering member, at a position distant from the projecting member by a predetermined distance.

With the above-described configuration, intensity of the near-infrared laser light beams at the condensing spot of the near-infrared laser light beams is uniform. Accordingly, by forming the image of the condensing spot at the position distant by the predetermined distance, an effect that intensity of projected light of an infrared projector is able to be uniform is achieved.

In an infrared projector according to an aspect 3 of the invention, it is preferable that, in the aspect 1 or 2, a moving mechanism (71) that adjusts relative positions of the projecting member and the scattering member is further included.

With the aforementioned configuration, it is possible to adjust the relative positions of the projecting member and the scattering member by the moving mechanism. Accordingly, an effect that a spread angle of the near-infrared laser light beam from the projecting member is able to be adjusted is achieved.

In an infrared projector according to an aspect 4 of the invention, it is preferable that, in any of the aspects 1 to 3, the scattering member is a member that includes a surface (front surface 51a) having predetermined roughness by which the entered near-infrared laser light beams are isotropically scattered.

With the aforementioned configuration, the near-infrared laser light beams received by the scattering member are isotropically scattered by unevenness provided in the surface having the predetermined roughness. Accordingly, an effect that the scattering member functions as a pseudo-light source is achieved.

In an infrared projector according to an aspect 5 of the invention, in any of the aspects 1 to 4, the scattering member may be made of metal.

In an infrared projector according to an aspect 6 of the invention, in any of the aspects 1 to 4, the scattering member may be made of ceramic.

In an infrared projector according to an aspect 7 of the invention, in any of the aspects 1 to 6, the plurality of near-infrared laser light beams may enter a predetermined surface of the scattering member, and the near-infrared laser light beams scattered to a side of the predetermined surface may be projected by the projecting member.

With the aforementioned configuration, the plurality of near-infrared laser light beams enter the predetermined surface of the scattering member. The infrared projector projects the near-infrared laser light beams, which are scattered to the side of the predetermined surface, by the projecting member. Accordingly, an effect that the surface of the scattering member, which the near-infrared laser light beams have entered, functions as a pseudo-light source is achieved.

In an infrared projector according to an aspect 8 of the invention, in any of the aspects 1 to 3, the scattering member (52) may be transparent to the near-infrared laser light beams.

With the aforementioned configuration, the scattering member is able to scatter the received near-infrared laser light beams to a side of a surface opposite to the receiving surface.

In an infrared projector according to an aspect 9 of the invention, in the aspect 8, the near-infrared laser light beams may be caused to enter a predetermined surface (front surface 52*a*) of the scattering member, and the near-infrared laser light beams scattered to a side of a surface (rear surface 52*b*) opposed to the predetermined surface may be projected by the projecting member.

With the aforementioned configuration, the plurality of near-infrared laser light beams enter the predetermined surface of the scattering member. The infrared projector projects the near-infrared laser light beams, which are scattered to the side of the surface opposed to the predetermined surface, by the projecting member. Accordingly, the scattering member functions as a pseudo-light source that emits the near-infrared laser light beams.

In an infrared projector according to an aspect 10 of the invention, in any of the aspects 1 to 3, the scattering member may be a light guiding member (53) that guides the near-infrared laser light beams.

With the aforementioned configuration, it is possible to mix the plurality of near-infrared laser light beams without using the scattering member.

In an infrared projector according to an aspect 11 of the invention, in the aspect 10, the plurality of near-infrared laser light beams may be caused to enter one end of the light guiding member, and the near-infrared laser light beams emitted from the other end may be projected by the projecting member.

With the aforementioned configuration, the plurality of near-infrared laser light beams enter the one end of the light guiding member. The infrared projector projects the near-infrared laser light beams, which are emitted from the other end, by the projecting member. Accordingly, an effect that the other end of the light guiding member functions as a pseudo-light source that emits the near-infrared laser light beams is achieved.

In an infrared projector according to an aspect 12 of the invention, in the aspect 10 or 11, the light guiding member may be a rod lens (light guiding member 53).

In an infrared projector according to an aspect 13 of the invention, in the aspect 10 or 11, the light guiding member may be a multimode fiber (light guiding member 54).

In an infrared projector according to an aspect 14 of the invention, in the aspect 11, the light guiding member may be formed so that an area of the one end is larger than an area of the other end.

With the aforementioned configuration, it is not necessary to condense the plurality of near-infrared laser light beams by a lens or the like for mixing them, so that an effect that the number of parts of the infrared projector is able to be reduced is achieved.

In an infrared projector according to an aspect 15 of the invention, in any of the aspects 1 to 14, the projecting member may be a lens (projecting member 61).

In an infrared projector according to an aspect 16 of the invention, in any of the aspects 1 to 14, the projecting member may be a concave mirror (projecting member 62).

In an infrared projector according to an aspect 17 of the invention, it is preferable that, in any of the aspects 1 to 16, each of peak wavelengths of the near-infrared laser light beams is not less than 740 nm and not more than 1000 nm.

It is preferable that an infrared observation system (1000) according to an aspect 18 of the invention includes: the infrared projector (100) according to any one of aspects 1 to 17; and a camera device (900) that captures an image formed by infrared rays projected from the infrared projector.

With the aforementioned configuration, in the infrared observation system, the camera device captures the image formed by the infrared rays projected from the infrared projector according to any of the aspects of the invention.

Thus, it is possible to capture a projected image in which moire resulting from unevenness of wavelengths in a projection pattern is reduced.

The invention is not limited to each of the embodiments described above, and may be modified in various manners within the scope indicated in the claims and an embodiment achieved by appropriately combining technical means disclosed in each of different embodiments is also encompassed in the technical scope of the invention. Further, by combining the technical means disclosed in each of the embodiments, a new technical feature may be formed.

Other Expressions of Invention

Note that, the invention is also able to be expressed as follows.

That is, a projector according to an aspect of the invention includes: a laser light source that emits a plurality of near-infrared laser light beams having different wavelengths; a scattering member that condenses the laser light beams and then scatters the resultant; and a projecting member that projects the laser light beams scattered by the scattering member.

In a projector according to an aspect of the invention, the projecting member forms an image of light distribution of the laser light beams, which is scattered by the scattering member, on the scattering member at a desired distance.

A projector according to an aspect of the invention is configured so as to be able to change relative positions of the projecting member and the scattering member.

In a projector according to an aspect of the invention, the relative positions of the scattering member and the projecting member are adjusted so that a spread angle θ of projected light from the projector becomes minimum.

In a projector according to an aspect of the invention, each of the wavelengths of the laser light source is any in a wavelength-band from 740 nm to 1000 nm.

In a projector according to an aspect of the invention, the scattering member is a member that has unevenness of a front surface thereof and is made of metal.

In a projector according to an aspect of the invention, the laser light beams enter a predetermined surface of the scattering member, and scattered light emitted to a side of the same surface as the entered surface is projected by the projecting member.

In a projector according to an aspect of the invention, the scattering member is a transparent member that the laser light beams pass through and are scattered by.

In a projector according to an aspect of the invention, the laser light beams enter a predetermined surface of the scattering member, and scattered light emitted to a side of a surface opposed to the entered surface is projected by the projecting member.

In a projector according to an aspect of the invention, the scattering member is a waveguide member that guides the laser light beams.

In a projector according to an aspect of the invention, the laser light beams enter one end of the scattering member, and the laser light beams emitted from the other end are projected by the projecting member.

In a projector according to an aspect of the invention, the scattering member is a multimode fiber.

In a projector according to an aspect of the invention, the scattering member is a rod lens.

In a projector according to an aspect of the invention, the scattering member is a slab waveguide.

In a projector according to an aspect of the invention, the projecting member is a lens.

In a projector according to an aspect of the invention, the projecting member is a concave mirror.

An observation system according to an aspect of the invention includes: any of the aforementioned projectors; and a camera device by which a projected image projected therefrom is observed.

INDUSTRIAL APPLICABILITY

The invention is able to be used for a projector that projects infrared rays, and a system by which an image formed by reflection of the infrared rays projected from the projector is observed.

REFERENCE SIGNS LIST 11a, 11b, 11c, 11d, 12a, 12b, 12c, 13a, 13b, 14a, 14b, 14c, 14d, 14e, 15a, 15b, 15c, 15d, 15e, 15f, 15g, 15h, 15i, 15j, 16a, 16b, 16c, 16d, 16e, 16f infrared semiconductor laser element (laser light source)
21a, 21b, 21c, 21d, 22a, 22b, 22c, 23a, 23b, 24a, 24b, 24c, 24d, 24e, 26a, 26b, 26c, 26d, 26e, 26f, 26g, 26h, 26i, 26j condenser lens
51, 52, 55 scattering member
53, 54, 56 light guiding member
61, 62, 63 projecting member
71, 72, 73, 74 moving mechanism
100, 200, 300, 400, 500, 600 infrared projector
900 camera device
1000 infrared observation system
L1a, L1b, L1c, L1d near-infrared laser light beam
IA, IB, IC condensing spot

The invention claimed is:

1. An infrared projector, comprising:
a plurality of laser light sources that emit near-infrared laser light beams;
a scattering member that receives the near-infrared laser light beams emitted from the plurality of laser light sources and scatters the received near-infrared laser light beams;
a light absorbing material surrounding the scattering member; and
a projecting member that projects the near-infrared laser light beams scattered by the scattering member, wherein
the near-infrared laser light beams are focused in an overlapping manner on a front surface of the scattering member.

2. The infrared projector according to claim 1, wherein the projecting member forms an image of a focused spot of the near-infrared laser light beams, which is formed on the scattering member, at a position distant from the projecting member by a predetermined distance.

3. The infrared projector according to claim 1, further comprising a moving mechanism that adjusts relative positions of the projecting member and the scattering member.

4. The infrared projector according to claim 1, wherein the scattering member is a member that includes a surface having predetermined roughness by which the entered near-infrared laser light beams are isotropically scattered.

5. The infrared projector according to claim 1, wherein the scattering member is made of metal.

6. The infrared projector according to claim 1, wherein the scattering member is made of ceramic.

7. The infrared projector according to claim 1, wherein the near-infrared laser light beams enter a predetermined surface of the scattering member, and the near-infrared laser light beams scattered to a side of the predetermined surface are projected by the projecting member.

8. The infrared projector according to claim 1, wherein the scattering member is transparent to the near-infrared laser light beams.

9. The infrared projector according to claim 8, wherein the near-infrared laser light beams are caused to enter a predetermined surface of the scattering member, and the near-infrared laser light beams scattered to a side of a surface opposed to the predetermined surface are projected by the projecting member.

10. The infrared projector according to claim 1, wherein the scattering member is a light guiding member that guides the near-infrared laser light beams.

11. The infrared projector according to claim 10, wherein the near-infrared laser light beams are caused to enter one end of the light guiding member, and the near-infrared laser light beams emitted from the other end are projected by the projecting member.

12. The infrared projector according to claim 10, wherein the light guiding member is a rod lens.

13. The infrared projector according to claim 10, wherein the light guiding member is a multimode fiber.

14. The infrared projector according to claim 11, wherein the light guiding member is formed so that an area of the one end is larger than an area of the other end.

15. The infrared projector according to claim 1, wherein the projecting member is a lens.

16. The infrared projector according to claim 1, wherein the projecting member is a concave mirror.

17. The infrared projector according to claim 1, wherein each of peak wavelengths of the near-infrared laser light beams is not less than 740 nm and not more than 1000 nm.

18. An infrared observation system, comprising:
the infrared projector according to claim 1; and
a camera device that captures an image formed by infrared rays projected from the infrared projector.

19. An infrared projector, comprising:
a plurality of laser light sources that emit near-infrared laser light beams;
a scattering member that receives the near-infrared laser light beams emitted from the plurality of laser light sources and scatters the received near-infrared laser light beams;
a light absorbing material surrounding the scattering member; and
a projecting member that projects the near-infrared laser light beams scattered by the scattering member, wherein
the near-infrared laser light beams enter the scattering member from directions that are different from each other.

20. An infrared projector, comprising:
a plurality of laser light sources that emit near-infrared laser light beams;
a scattering member that receives the near-infrared laser light beams emitted from the plurality of laser light sources and scatters the received near-infrared laser light beams;
a light absorbing material surrounding the scattering member;

a projecting member that projects the near-infrared laser light beams scattered by the scattering member; and an optical transmission path that transmits the near-infrared laser light beams in a mixed manner.

* * * * *